US008663926B2

(12) United States Patent
Boyer et al.

(10) Patent No.: US 8,663,926 B2
(45) Date of Patent: Mar. 4, 2014

(54) DETECTION OF ANTHRAX PATHOGENICITY FACTORS

(75) Inventors: Anne E. Boyer, Atlanta, GA (US); Conrad P. Quinn, Lilburn, GA (US); John R. Barr, Suwanee, GA (US)

(73) Assignee: The United States of America, as represented by the Secretary, Department of Health and Human Services, Centers for Disease Control and Prevention, Washington, DC (US)

( * ) Notice: Subject to any disclaimer, the term of this patent is extended or adjusted under 35 U.S.C. 154(b) by 2033 days.

(21) Appl. No.: 11/675,233

(22) Filed: Feb. 15, 2007

(65) Prior Publication Data
US 2012/0122123 A1 May 17, 2012

Related U.S. Application Data

(60) Provisional application No. 60/773,489, filed on Feb. 15, 2006.

(51) Int. Cl.

| | |
|---|---|
| *C12Q 1/68* | (2006.01) |
| *C12Q 1/00* | (2006.01) |
| *C12N 5/00* | (2006.01) |
| *C12N 5/02* | (2006.01) |
| *A61K 49/00* | (2006.01) |
| *A61K 39/07* | (2006.01) |
| *A61B 5/00* | (2006.01) |
| *A61B 8/00* | (2006.01) |
| *A61B 10/00* | (2006.01) |
| *A01N 63/00* | (2006.01) |

(52) U.S. Cl.
USPC ............... 435/6.15; 435/4; 435/325; 424/9.1; 424/246.1; 424/9.6; 424/93.46

(58) Field of Classification Search
None
See application file for complete search history.

(56) References Cited

U.S. PATENT DOCUMENTS

| | | | | |
|---|---|---|---|---|
| 7,410,769 | B2 * | 8/2008 | Burroughs-Tencza | 435/7.1 |
| 7,504,202 | B2 * | 3/2009 | Cullum et al. | 435/4 |
| 7,670,796 | B2 * | 3/2010 | Shone et al. | 435/23 |
| 2002/0076741 | A1 * | 6/2002 | Tencza | 435/23 |
| 2009/0048293 | A1 * | 2/2009 | Popov et al. | 514/312 |
| 2010/0298390 | A1 * | 11/2010 | Pellecchia et al. | 514/369 |

FOREIGN PATENT DOCUMENTS

| | | |
|---|---|---|
| WO | WO-03/040384 | 5/2003 |
| WO | WO-03073066 | 9/2003 |

OTHER PUBLICATIONS

Haukanes et al., Bio/Technology, 1993; 11: 60-63.*
Seger et al., The Journal of Biological Chemistry, 1992; 267(36): 25628-2563.*
Mock, Michael et al., "Progress in rapid screening of *Bacillus anthracis* lethal factor acitivity"; PNAS, May 14, 2002, vol. 99, No. 10, 6527-6529.
Mourez, Michael et al., "Designing a polyvalent inhibitor of anthrax toxin", Nature Biotechnology, vol. 19, Oct. 2001, pp. 958-961.
Cummings, Richard T. et al., "A peptide-based fluorescence resonance energy transfer assay for *Bacillus anthracis* lethal factor protease", PNAS, May 14, 2002, vol. 99, No. 10, pp. 6603-6606.
Rivera, Victor R. et al., "An enzymatic electrochemiluminescence assay for the lethal factor of anthrax", Academic Press, Analytical Biochemistry, 321 (2003) pp. 125-130.
Kim, Joungmok et al., "Production and proteolytic assay of lethal factor from *Bacillus anthracis*", Acadmic Press, Science Direct, Protein Expression and Purification 30 (2003) pp. 293-300.
Tonello, Florella et al., "The Metalloproteolytic Activity of the Anthras Lethal Factor Is Substrate-inhibited", The Journal of Biological Chemistry, vol. 278, No. 41, Issue of Oct. 10, pp. 40075-40078, 2003.
Turk, Benjamin E. et al., "The structural basis for substrate and inhibitor selectivity of the anthrax lethal factor", vol. 11, No. 1, Jan. 2004, Nature Structural & Molecular Biology, pp. 60-66.
Panchal, Rekha G. et al., "Identification of small molecule inhibitors of anthrax lethal factor", Nature Structural & Molecular Biology, vol. 11, No. 1, Jan. 2004.
Mock, Michele et al., "Progress in rapid screening of *Bacillus anthracis* lethal factor activity", PNAS, May 14, 2002, vol. 99, No. 10, pp. 6527-6529.
Rivera, Victor R. et al., "An enzymatic electrochemiluminescence assay for the lethal factor of anthrax", Academic Press, Analytical Biochemistry, 321 (2003), pp. 125-130.
Boyer, A. et al., Detection and Quantification of Anthrax Lethal Factor in Serum by Mass Spectrometry, *Analytical Chermistry*, 79(22): 8463-70, Nov. 15, 2007.
Hammond, S. et al., Lethal Factor Active-Site Mutations Affect Catalytic Activity in Vitro, *Infection and Immunity*, 66(5): 2374-78, May 1998.

(Continued)

*Primary Examiner* — Vanessa L Ford
*Assistant Examiner* — Lakia Tongue
(74) *Attorney, Agent, or Firm* — Gifford, Krass, Sprinkle, Anderson & Citkowski, P.C.

(57) ABSTRACT

One major problem in diagnosis methods presently available for anthrax is that these methods require several days to produce a result. The only existing treatment for anthrax requires administration soon after infection at a time when patients are exhibiting only mild flu-like symptoms. Thus, a patient may be days beyond the time when treatment would be effective by the time a diagnosis is made. The present invention reduces diagnosis time to as little as four hours providing same day identification of anthrax radically increasing the odds of delivering proper treatment and patient recovery. The rapid identification of anthrax lethal factor activity exhibited by the instant invention is also amenable to in vivo screening protocols for the discovery and development of anthrax vaccines and lethal factor inhibitors. The instant invention isolates and concentrates lethal factor and lethal toxin from nearly any biological sample. By capitalizing on the endopeptidase activity of lethal factor the present invention amplifies output signals producing reliable detection of picomolar concentrations of lethal factor. The instant invention involves novel purification and detection techniques and substrates for rapid, reproducible, and quantitative measurements of anthrax lethal factor in biological samples.

20 Claims, 15 Drawing Sheets

(56) References Cited

OTHER PUBLICATIONS

Harlow, E. et al., Antibodies A Laboratory Manual, US Cold Spring Harbor Laboratory, pp. 511-552, 1988.

Mabry, R. et al., Detection of anthrax toxin in the serum of animals infected with *Bacillus anthracis* by using engineered immunoassays, *Clinical and Vaccine Immunology*, 13(6): 671-77, Jun. 2006.

Matayoshi, E. et al., Novel Fluorogenic Substrates for Assaying Retroviral Proteases by Resonance Energy Transfer, *Science*, 247: 954-958, 1990.

Tonello, F. et al., Screening inhibitors of anthrax lethal factor, *Nature*, 418: 386, and supplemental information, Jul. 25, 2002.

Walsh, J. et al., A case of naturally acquired inhalation anthrax: clinical care and analyses of anti-protective antigen immunoglobulin G and lethal factor, *Clinical Infectious Diseases: An Official Publication of the Infectious Diseases Society of America*, 44(7): 968-71, Apr. 1, 2007.

\* cited by examiner

Fig. 1

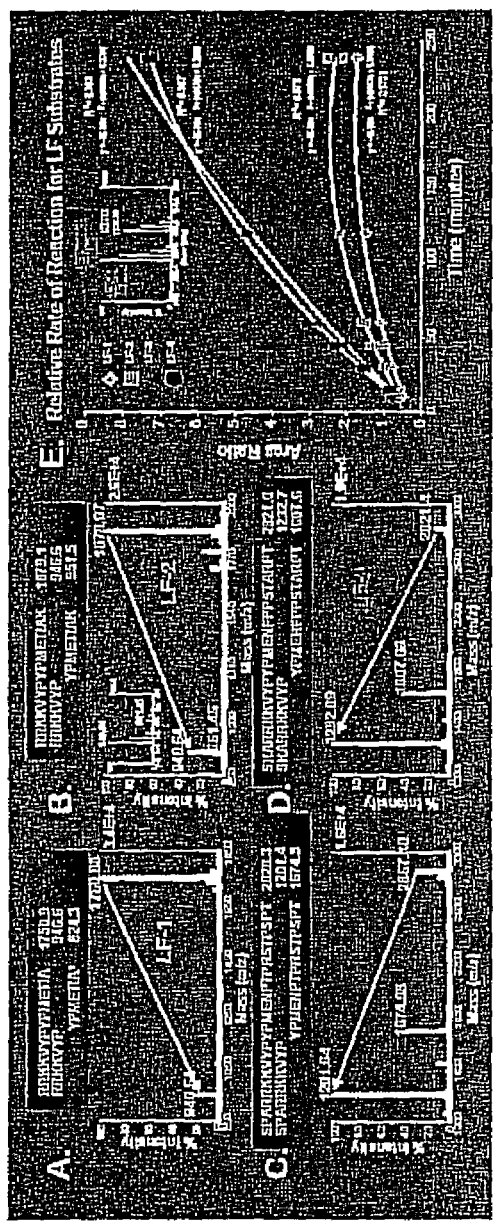
FIG. 4 A-E

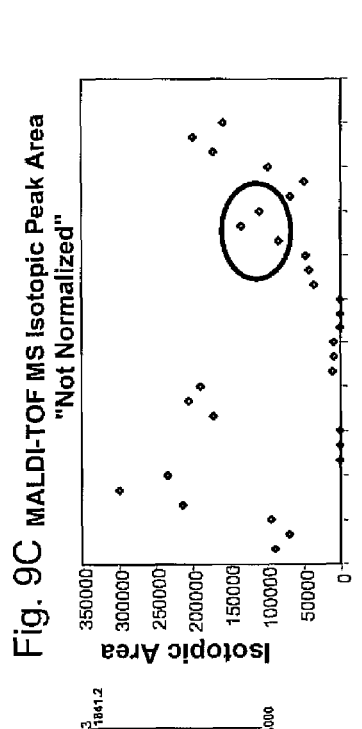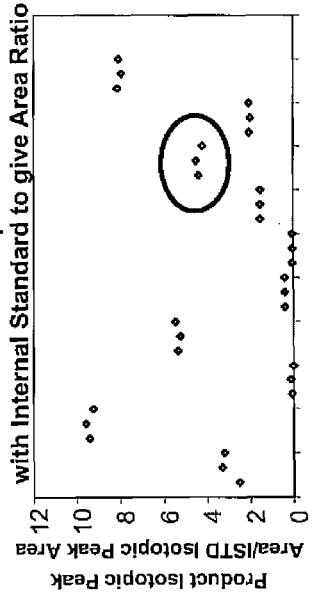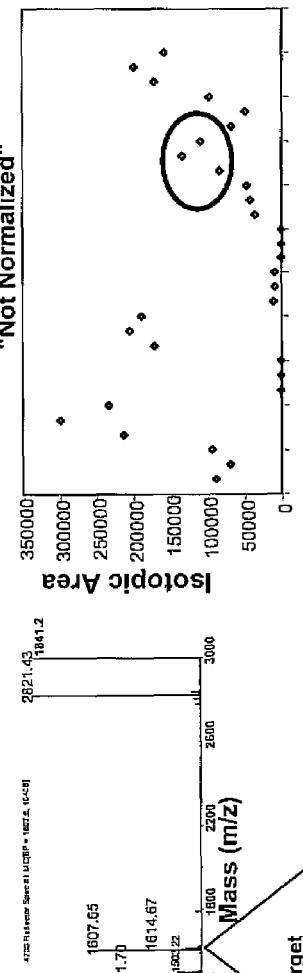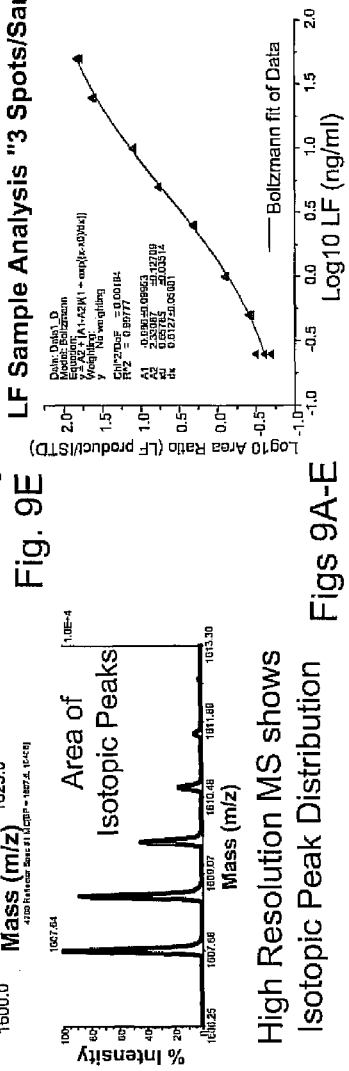
Figs 9A-E

Fig. 10

Application to Infection Sera

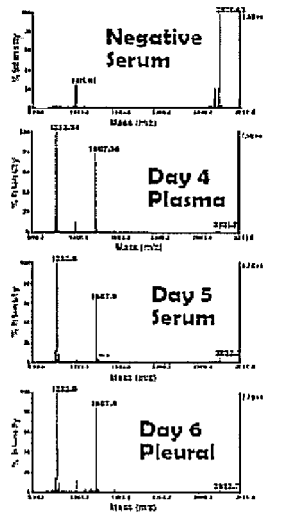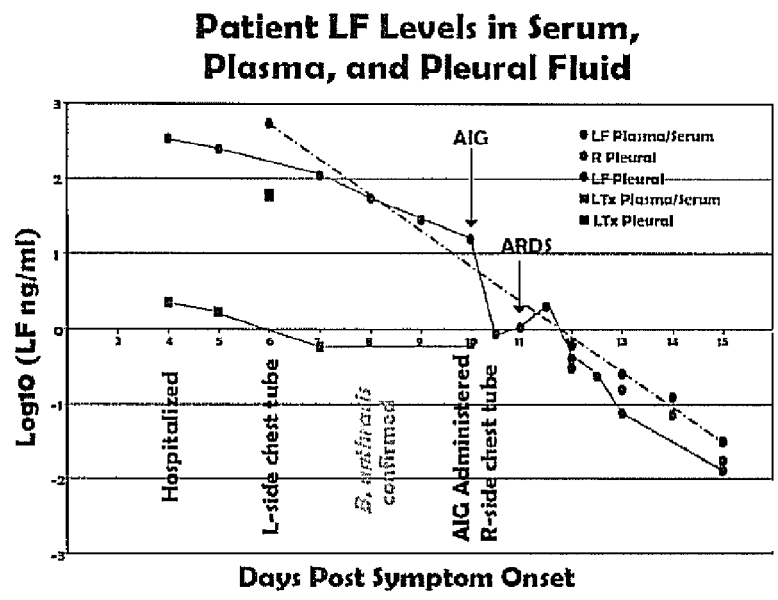
FIG. 13

SEQUENCE LISTING

```
<160> NUMBER OF SEQ ID NOS: 18

<210> SEQ ID NO 1
<211> LENGTH: 22
<212> TYPE: PRT
<213> ORGANISM: Artificial Sequence
<220> FEATURE:
<223> OTHER INFORMATION: peptide substrate cleaved by anthrax
      pathogenicity factor

<400> SEQUENCE: 1

Ser Lys Ala Arg Arg Lys Lys Val Tyr Pro Met Glu Asn Phe Pro Pro
1               5                   10                  15

Ser Thr Ala Arg Pro Thr
            20
```

```
<210> SEQ ID NO 2
<211> LENGTH: 14
<212> TYPE: PRT
<213> ORGANISM: Artificial Sequence
<220> FEATURE:
<223> OTHER INFORMATION: peptide substrate cleaved by anthrax
      pathogenicity factor

<400> SEQUENCE: 2

Arg Arg Lys Lys Val Tyr Pro Tyr Pro Met Glu Thr Ile Ala
1               5                   10

<210> SEQ ID NO 3
<211> LENGTH: 15
<212> TYPE: PRT
<213> ORGANISM: Artificial Sequence
<220> FEATURE:
<223> OTHER INFORMATION: peptide substrate cleaved by anthrax
      pathogenicity factor

<400> SEQUENCE: 3

Arg Arg Lys Lys Val Tyr Pro Tyr Pro Met Glu Thr Ile Ala Lys
1               5                   10                  15

<210> SEQ ID NO 4
<211> LENGTH: 25
<212> TYPE: PRT
<213> ORGANISM: Artificial Sequence
<220> FEATURE:
<223> OTHER INFORMATION: peptide substrate cleaved by anthrax
      pathogenicity factor

<400> SEQUENCE: 4

Ser Pro Ala Arg Arg Lys Lys Val Tyr Pro Tyr Pro Met Glu Asn Pro
1               5                   10                  15

Thr Pro Arg Ser Thr Pro Ser Pro Thr
            20                  25

<210> SEQ ID NO 5
<211> LENGTH: 24
<212> TYPE: PRT
<213> ORGANISM: Artificial Sequence
<220> FEATURE:
<223> OTHER INFORMATION: peptide substrate cleaved by anthrax
      pathogenicity factor

<400> SEQUENCE: 5

Ser Lys Ala Arg Arg Lys Lys Val Tyr Pro Tyr Pro Met Glu Asn Phe
1               5                   10                  15

Pro Pro Ser Thr Ala Arg Pro Thr
            20

<210> SEQ ID NO 6
<211> LENGTH: 16
<212> TYPE: PRT
<213> ORGANISM: Artificial Sequence
<220> FEATURE:
<223> OTHER INFORMATION: peptide substrate cleaved by anthrax
      pathogenicity factor
<220> FEATURE:
<221> NAME/KEY: MISC_FEATURE
<222> LOCATION: (1)..(1)
<223> OTHER INFORMATION: X is norleucine

<400> SEQUENCE: 6

Xaa Lys Lys Lys Lys Val Leu Pro Ile Gln Leu Asn Ala Ala Thr Asp
1               5                   10                  15
```

```
<210> SEQ ID NO 7
<211> LENGTH: 16
<212> TYPE: PRT
<213> ORGANISM: Artificial Sequence
<220> FEATURE:
<223> OTHER INFORMATION: peptide substrate cleaved by anthrax
      pathogenicity factor
<220> FEATURE:
<221> NAME/KEY: MISC_FEATURE
<222> LOCATION: (1)..(1)
<223> OTHER INFORMATION: 5,6-carboxyfluoresceinyl

<400> SEQUENCE: 7

Met Pro Lys Lys Lys Pro Thr Pro Ile Gln Leu Asn Pro Ala Pro Asp
1               5                   10                  15

<210> SEQ ID NO 8
<211> LENGTH: 19
<212> TYPE: PRT
<213> ORGANISM: Artificial Sequence
<220> FEATURE:
<223> OTHER INFORMATION: peptide substrate cleaved by anthrax
      pathogenicity factor
<220> FEATURE:
<221> NAME/KEY: MISC_FEATURE
<222> LOCATION: (1)..(1)
<223> OTHER INFORMATION: X is norleucine
<220> FEATURE:
<221> NAME/KEY: MISC_FEATURE
<222> LOCATION: (1)..(1)
<223> OTHER INFORMATION: 5,6-carboxyfluoresceinyl

<400> SEQUENCE: 8

Xaa Pro Lys Lys Lys Pro Thr Pro Ile Gln Leu Asn Pro Ala Pro Asp
1               5                   10                  15

Lys Gly Gly

<210> SEQ ID NO 9
<211> LENGTH: 19
<212> TYPE: PRT
<213> ORGANISM: Artificial Sequence
<220> FEATURE:
<223> OTHER INFORMATION: peptide substrate cleaved by anthrax
      pathogenicity factor
<220> FEATURE:
<221> NAME/KEY: MISC_FEATURE
<222> LOCATION: (1)..(1)
<223> OTHER INFORMATION: X is norleucine
<220> FEATURE:
<221> NAME/KEY: MISC_FEATURE
<222> LOCATION: (1)..(1)
<223> OTHER INFORMATION: 5,6-carboxyfluoresceinyl

<400> SEQUENCE: 9

Xaa Lys Lys Lys Lys Val Leu Pro Ile Gln Leu Asn Ala Ala Thr Asp
1               5                   10                  15

Lys Gly Gly

<210> SEQ ID NO 10
<211> LENGTH: 19
<212> TYPE: PRT
<213> ORGANISM: Artificial Sequence
<220> FEATURE:
<223> OTHER INFORMATION: peptide substrate cleaved by anthrax
      pathogenicity factor
<220> FEATURE:
<221> NAME/KEY: MISC_FEATURE
<222> LOCATION: (1)..(1)
<223> OTHER INFORMATION: X is norleucine
<220> FEATURE:
<221> NAME/KEY: MISC_FEATURE
```

```
<222> LOCATION: (1)..(1)
<223> OTHER INFORMATION: 7-hydroxy-4-methyl-3-acetylcoumarinyl
<220> FEATURE:
<221> NAME/KEY: MISC_FEATURE
<222> LOCATION: (17)..(17)
<223> OTHER INFORMATION: N-({4-[(7-nitro-2,1,3-benzoxadiazol-4-yl)amino]
      phenyl}acetyl

<400> SEQUENCE: 10

Xaa Lys Lys Lys Lys Val Leu Pro Ile Gln Leu Asn Ala Ala Thr Asp
1               5                   10                  15

Lys Gly Gly

<210> SEQ ID NO 11
<211> LENGTH: 19
<212> TYPE: PRT
<213> ORGANISM: Artificial Sequence
<220> FEATURE:
<223> OTHER INFORMATION: peptide substrate cleaved by anthrax
      pathogenicity factor
<220> FEATURE:
<221> NAME/KEY: MISC_FEATURE
<222> LOCATION: (1)..(1)
<223> OTHER INFORMATION: X is norleucine
<220> FEATURE:
<221> NAME/KEY: MISC_FEATURE
<222> LOCATION: (1)..(1)
<223> OTHER INFORMATION: 7-hydroxy-4-methyl-3-acetylcoumarinyl
<220> FEATURE:
<221> NAME/KEY: MISC_FEATURE
<222> LOCATION: (17)..(17)
<223> OTHER INFORMATION: 4 dimethylaminoazobenzene-4'-carboxyl

<400> SEQUENCE: 11

Xaa Lys Lys Lys Lys Val Leu Pro Ile Gln Leu Asn Ala Ala Thr Asp
1               5                   10                  15

Lys Gly Gly

<210> SEQ ID NO 12
<211> LENGTH: 19
<212> TYPE: PRT
<213> ORGANISM: Artificial Sequence
<220> FEATURE:
<223> OTHER INFORMATION: peptide substrate cleaved by anthrax
      pathogenicity factor
<220> FEATURE:
<221> NAME/KEY: MISC_FEATURE
<222> LOCATION: (1)..(1)
<223> OTHER INFORMATION: X is norleucine
<220> FEATURE:
<221> NAME/KEY: MISC_FEATURE
<222> LOCATION: (1)..(1)
<223> OTHER INFORMATION: N-({4-[(7-nitro-2,1,3-benzoxadiazol-4-yl)
      amino]phenyl}acetyl
<220> FEATURE:
<221> NAME/KEY: MISC_FEATURE
<222> LOCATION: (17)..(17)
<223> OTHER INFORMATION: 7-hydroxy-4-methyl-3-acetylcoumarinyl

<400> SEQUENCE: 12

Xaa Lys Lys Lys Lys Val Leu Pro Ile Gln Leu Asn Ala Ala Thr Asp
1               5                   10                  15

Lys Gly Gly

<210> SEQ ID NO 13
<211> LENGTH: 19
<212> TYPE: PRT
<213> ORGANISM: Artificial Sequence
<220> FEATURE:
<223> OTHER INFORMATION: peptide substrate cleaved by anthrax
      pathogenicity factor
```

```
<220> FEATURE:
<221> NAME/KEY: MISC_FEATURE
<222> LOCATION: (1)..(1)
<223> OTHER INFORMATION: X is norleucine
<220> FEATURE:
<221> NAME/KEY: MISC_FEATURE
<222> LOCATION: (1)..(1)
<223> OTHER INFORMATION: 4 dimethylaminoazobenzene-4'-carboxyl
<220> FEATURE:
<221> NAME/KEY: MISC_FEATURE
<222> LOCATION: (17)..(17)
<223> OTHER INFORMATION: 7-hydroxy-4-methyl-3-acetylcoumarinyl

<400> SEQUENCE: 13

Xaa Lys Lys Lys Lys Val Leu Pro Ile Gln Leu Asn Ala Ala Thr Asp
1               5                   10                  15

Lys Gly Gly

<210> SEQ ID NO 14
<211> LENGTH: 15
<212> TYPE: PRT
<213> ORGANISM: Artificial Sequence
<220> FEATURE:
<223> OTHER INFORMATION: peptide substrate cleaved by anthrax
      pathogenicity factor

<400> SEQUENCE: 14

Arg Arg Lys Lys Val Tyr Pro Tyr Pro Met Glu Pro Thr Ile Ala
1               5                   10                  15

<210> SEQ ID NO 15
<211> LENGTH: 24
<212> TYPE: PRT
<213> ORGANISM: Artificial Sequence
<220> FEATURE:
<223> OTHER INFORMATION: peptide substrate cleaved by anthrax
      pathogenicity factor
<220> FEATURE:
<221> NAME/KEY: MISC_FEATURE
<222> LOCATION: (13)..(13)
<223> OTHER INFORMATION: X is norleucine

<400> SEQUENCE: 15

Ser Lys Ala Arg Arg Lys Lys Val Tyr Pro Tyr Pro Xaa Glu Asn Phe
1               5                   10                  15

Pro Pro Ser Thr Ala Arg Pro Thr
            20

<210> SEQ ID NO 16
<211> LENGTH: 22
<212> TYPE: PRT
<213> ORGANISM: Artificial Sequence
<220> FEATURE:
<223> OTHER INFORMATION: peptide substrate cleaved by anthrax
      pathogenicity factor
<220> FEATURE:
<221> NAME/KEY: MISC_FEATURE
<222> LOCATION: (1)..(1)
<223> OTHER INFORMATION: MCA
<220> FEATURE:
<221> NAME/KEY: MISC_FEATURE
<222> LOCATION: (13)..(13)
<223> OTHER INFORMATION: X is norleucine
<220> FEATURE:
<221> NAME/KEY: MISC_FEATURE
<222> LOCATION: (22)..(22)
<223> OTHER INFORMATION: DNP

<400> SEQUENCE: 16

Ser Lys Ala Arg Arg Lys Lys Val Tyr Pro Tyr Pro Xaa Glu Asn Phe
1               5                   10                  15
```

```
Pro Pro Ser Thr Ala Arg
            20

<210> SEQ ID NO 17
<211> LENGTH: 22
<212> TYPE: PRT
<213> ORGANISM: Artificial Sequence
<220> FEATURE:
<223> OTHER INFORMATION: peptide substrate cleaved by anthrax
      pathogenicity factor
<220> FEATURE:
<221> NAME/KEY: MISC_FEATURE
<222> LOCATION: (1)..(1)
<223> OTHER INFORMATION: oAbz
<220> FEATURE:
<221> NAME/KEY: MISC_FEATURE
<222> LOCATION: (13)..(13)
<223> OTHER INFORMATION: X is norleucine
<220> FEATURE:
<221> NAME/KEY: MISC_FEATURE
<222> LOCATION: (22)..(22)
<223> OTHER INFORMATION: DNP

<400> SEQUENCE: 17

Ser Lys Ala Arg Arg Lys Lys Val Tyr Pro Tyr Pro Xaa Glu Asn Phe
1               5                   10                  15

Pro Pro Ser Thr Ala Arg
            20

<210> SEQ ID NO 18
<211> LENGTH: 24
<212> TYPE: PRT
<213> ORGANISM: Artificial Sequence
<220> FEATURE:
<223> OTHER INFORMATION: peptide substrate cleaved by anthrax
      pathogenicity factor
<220> FEATURE:
<221> NAME/KEY: MISC_FEATURE
<222> LOCATION: (24)..(24)
<223> OTHER INFORMATION: FITC-DABCYL

<400> SEQUENCE: 18

Ser Lys Ala Arg Arg Lys Lys Val Tyr Pro Tyr Pro Met Glu Asn Phe
1               5                   10                  15

Pro Pro Ser Thr Ala Arg Pro Thr
            20
```

DETECTION OF ANTHRAX PATHOGENICITY FACTORS

RELATED APPLICATIONS

This application claims priority of U.S. Provisional Patent Application Ser. No. 60/773,489 filed Feb. 15, 2006, which is incorporated herein by reference.

GOVERNMENT INTEREST

The invention described herein may be manufactured, used, and licensed by or for the United States Government.

FIELD OF THE INVENTION

The invention relates generally to disease diagnostics, and in particular to methods for detecting infection of anthrax in a patient and screening anthrax therapeutics.

BACKGROUND OF THE INVENTION

Anthrax is caused by infection with *Bacillus anthracis*, a spore-forming, rod-shaped bacterium. The dormant spore-form is highly resistant to extreme conditions, high temperatures, and a variety of chemical treatments. The spores gain entry either through an open wound, causing cutaneous disease, or by ingestion, causing gastrointestinal disease or are inhaled causing inhalation anthrax. All three forms can progress to a systemic infection leading to shock, respiratory failure, and death. (Mock, M. and Mignot, T. (2003), *Cell Microbiol.*, 5(1):15-23). The stability of the spores and their infectious capacity make them a convenient bioterrorist weapon.

The two known toxins of *B. anthracis* are binary combinations of protective antigen (PA), named for its ability to induce protective immunity against anthrax, with either edema factor (EF) or lethal factor (LF). PA is the cell binding component of both toxins and is responsible for bringing the catalytic EF or LF into the host cells. EF is an adenylate cyclase which converts ATP to cyclic AMP and causes edema (Brossier, F. and Mock, M. (2001), *Toxicon.* 39(11):1747-55). The combination of PA-EF forms edema toxin (ETx) which causes edema when injected locally. LF is a zinc-dependent endoprotease known to target the amino-terminus of the mitogen-activated protein kinase kinase (MAPKK) family of response regulators (Id.). The cleavage of these proteins disrupts a signaling pathway and leads to cytokine dysregulation and immune dysfunction. LF combined with PA forms lethal toxin (LTx) which is lethal when injected on its own. It is also known that there are fatal anthrax cases where administration of antibiotics and clearance of bacteria have failed to rescue the patient. This indicates that there may be a "point of no return" level of LTx in the blood that may predict the outcome of infection. Clearly, LTx and its components are important targets for diagnostics and quantification.

The protein targets of LF are highly specific, and peptides similar to those proteins can be used as artificial substrates. The inventive method uses an artificial peptide substrate which is clipped by LF producing two distinct smaller peptide products. The LF specific cleaved peptides are detected by a variety of rapid quantitative methods illustratively including matrix assisted laser desorption ionization time of flight mass spectrometry (MALDI-TOF) that visualizes mass specific peaks of the cleaved peptides and fluorescence resonance energy transfer (FRET) that allows for simple detection using bench top fluorometers. Thus, the instant invention detects the specific activity of LF by measuring peptide cleavage products produced per unit time to indicate the amount of LF present.

Existing assays for LF activity, such as SDS-PAGE (Vitale, G. et al. (2000), *Biochem. J.*, 352:739-745; Duesbery, N. S. et al. (1998), *Science*, 280, 734-737) or HPLC (Hammond, S. E., Hanna, P. C. (1998), *Infect. Immun.*, 66:2374-2378), are impractical for high-throughput screening of compound collections and rapid diagnosis of host infection. Methods for rapid screening of patients in a hospital setting or identification of potent and selective LF inhibitors requires an assay that is less labor intensive, has faster turnaround, and is effective at low levels of enzyme. (Cummings, R. T. (2002), *PNAS*, 99:6603-6606).

Development of a safe and effective vaccine for inhalation and other forms of anthrax infection is vital to the health and safety of the population and an essential component of any bioterrorism defense strategy. Additionally, the identification of targeted therapies following anthrax infection is essential to managing a patient population. As such, there exists a need for methods to rapidly identify possible candidate vaccines and treatments. There also exists a need for rapid diagnosis of anthrax infection that can be distinguished from other infections that initially display similar symptoms.

SUMMARY OF THE INVENTION

The instant invention teaches a method for detecting an anthrax pathogenicity factor in a biological sample. The anthrax pathogenicity factor is isolated and concentrated from the biological sample. The anthrax pathogenicity factor is subsequently reacted with a peptide substrate that is cleaved to yield at least two substrate cleavage products detected by one of several methods known in the art. As such, relative catalytic efficiency of the anthrax pathogenicity factor is measured.

Multiple forms of anthrax pathogenicity factor are taught by and are detected by the present invention illustratively including *Bacillus anthracis* lethal factor and *Bacillus anthracis* lethal toxin.

The instant invention teaches a biological sample that is acquired by standard methods known in the art from a patient or other test subject illustratively including humans and other mammals. The biological sample illustratively includes whole blood, plasma, serum, extracellular fluid, cytosolic fluid, pleural fluid, or tissue.

A target form of anthrax pathogenicity factor is isolated and concentrated from the biological sample in an exemplary step through binding to beads coupled with an antibody specific to the anthrax pathogenicity factor. The beads employed are optionally magnetic, thereby allowing for gentle and rapid separation from other components present in the biological sample. The isolation and purification substrate occurs on a solid substrate or other substrates known in the art. A solid substrate is illustratively a microtiter plate. Magnetic beads are optionally coated with protein G and an antibody specific to the anthrax pathogenicity factor. Antibodies operative herein illustratively include those derived from organisms including mammal, human, mouse, rabbit, monkey, donkey, horse, rat, swine, cat, chicken, goat, guinea pig, hamster, and sheep. The antibody selected is appreciated to be monoclonal or polyclonal. Antibodies specific for various targets are employed illustratively including anthrax protective antigen, lethal toxin, lethal factor and edema factor.

Following isolation and concentration, the pathogenicity factor is reacted with a peptide substrate to determine the enzymatic activity specific for pathogenicity factor present in the biological sample. The instant invention teaches synthetic forms of a peptide substrate that contain between 2 and 100 residues. However, it is appreciated that large protein substrates such as members of the mitogen-activated protein kinase kinase family are also operative herein. The peptide substrate optionally is tagged with one or more detection taggant molecules to facilitate detection, the taggants illustratively including a fluorophore, a fluorescence quenching molecule, or a light-absorbing molecule, biotin, avidin, horseradish peroxidase, streptavidin, and digoxin. Nonlimiting examples of peptide substrates operative in the present invention include sequence numbers Seq. Nos. 1-18.

The instant invention teaches several detection methods, illustratively including mass spectrometry, fluorescence resonance energy transfer, fluorescence, light absorption, enzyme linked immunoadsorbant assay, coupled enzyme assay, continuous enzyme assay, discontinuous enzyme assay, flow cytometry, FLIPR, high-performance liquid chromatography, and colorimetric assay.

The instant invention also teaches an apparatus for isolating and detecting an anthrax pathogenicity factor that includes isolation and concentration of the pathogenicity factor by binding to magnetic beads. The apparatus includes a reaction chamber in which the isolated and concentrated pathogenicity factor is reacted with a peptide substrate that is subsequently applied to a matrix-assisted laser desorption ionization time of flight mass spectrometer (MALDI-TOF) apparatus for detection and quantification of cleavage products.

BRIEF DESCRIPTION OF THE DRAWINGS

FIG. 1 is a schematic of *Bacillus anthracis* binary toxins that include lethal toxin which is assembled from the zinc-dependent endopeptidase lethal factor and the receptor bind protein protective antigen (PA) that also serves as the receptor binding component of edema toxin formed through assembly with edema factor.

FIG. 4 cumulatively depicts a comparison of peptide substrates. FIG. 4A is a mass spectrum for substrate LF-1 that is based on a FRET substrate optimized by Turk et al. (2004), *Nat. Struc. Mol. Biol.*, 11:60-66); FIG. 4B is a mass spectrum for substrate LF-2 that includes one additional lysine on the carboxy-terminus; FIGS. 4C and 4D are mass spectra for substrates LF-3 and LF-4 respectively that include 10 additional amino acids based on the extended consensus sequence of MAPKK. For these reactions 10 ng LF is incubated with 5 nmoles of each substrate in 200 µl buffer for 2 hours at 37° C., sampled at times 5, 10, 15, 30, 45, 60, 90, 120, and 240 minutes for MALDI-TOF analysis with relative quantification. At 120 minutes, 1 µl of each reaction is analyzed without internal standard (ISTD) peptides to acquire the spectra shown in FIGS. 4A-D. FIG. 4E is a plot of the area ratio of the peaks for the amino terminal product peptides of FIGS. 4A-4B relative to an ISTD peptide over time giving the relative rates of reaction for each peptide.

FIG. 7 depicts through mass spectra a comparison of LF antibody efficiency for LF cleavage with the 1607 m/z LF cleaved peptide being a quantitative target, the relative assay sensitivity for LF mAb, rabbit Ab, and macaque Ab is provided.

FIG. 8 is mass spectra indicating LF activity is higher with PA-LF (LTx) and LF-mAb complexes relative to uncomplexed LF as determined by relative intensity of the LF cleavage product (m/z≈1607) relative to intact substrate of Seq. No. 1 (m/z≈2821); FIG. 8A is the spectrum for 500 pg of LF-PA (LTx) in buffer in the presence of substrate Seq. No. 1 and absent MABs; FIG. 8B is the spectrum for 500 pg of LF retrieved with LF MABs then mixed with buffer and in the presence of substrate Seq. No. 1; and FIG. 8C is the spectrum for 500 pg of LF in buffer in the presence of substrate Seq. No. 1 and absent MABs.

FIG. 9A is a mass spectrum of the LF cleavage reaction showing peaks representing the peptide substrate and two products; FIG. 9B is mass spectra of the LF cleaved peptide of mass 1607 m/z as the quantitative target with an isotopically labeled peptide of 7 mass units higher than the target (at 1614 m/z) added as an internal standard to normalize spot to spot signal intensity differences. Narrowing the x-axis shows the isotopic distribution associated with both peptides; FIG. 9C is a plot as a function of area for 3 spots from one sample indicating the varied intensity differences, with the areas of the LF peptide for triplicate spots for a variety of samples being plotted "not normalized"; FIG. 9D is a plot of the area of the isotopic peaks for the 1607 m/z LF-specific "target" analyte divided by the area isotopic peaks of the labeled internal standard that gives the area ratio which allows absolute quantitation when plotted as a function of concentration and "normalizes" the spot to spot area differences; FIG. 9E is a plot of the $Log_{10}$ of LF in ng/ml versus the $Log_{10}$ of the Area Ratio, a sigmoidal fit and interpolation allows calculation of LF concentration.

FIG. 10 is a bar graph depicting relative activity differences between LF and LTx in the presence and absence of targeted antibodies.

FIG. 11A is a plot of table of survival times for three separate macaques after *B. anthracis* spore inhalation as noted by circles (upper left panel), a mass spectrum of an animal prior to infection (lower left panel), and mass spectra for each animal based on 5 µl of serum collected on day 2 post infection showing higher LF levels at day 2 in animals that survive longer; animal 1 shows the shortest time to mortality which correlates with the lowest level of LF activity. Animal 3 shows the longest time to mortality with a correspondingly high level of serum LF activity. FIG. 11B is a comparison of total LF and LTx activity in serum taken at days 2 and 3 from animal 2 of FIG. 11A; and FIG. 11C is a comparison of LF and LTx levels at day 2 post infection and at death for all three animals, with levels of LTx increasing relative to LF as the infection progresses and upon occurrence of death.

FIG. 13 depicts representative MALDI-TOF mass spectra in descending order from a human patient on a first day of hospitalization with serum negative for LF; day 4 post symptomatic (PS) from plasma; day 5 PS from serum; day 6 from pleural fluid (left panel). A plot (right panel) of LF and LTx as a function of days PS onset for serum, plasma, and pleural fluid from the human patient, with disease progression events noted. LF levels in excess of 100 ng/ml are identified in patient plasma/serum upon hospitalization at day 4 following onset of symptoms. Standard diagnostic techniques confirm anthrax infection at day 8. LF levels in serum/plasma and pleural fluid fall at similar rates from day 4 to day 15.

DETAILED DESCRIPTION OF THE PREFERRED EMBODIMENTS

Figure 2:
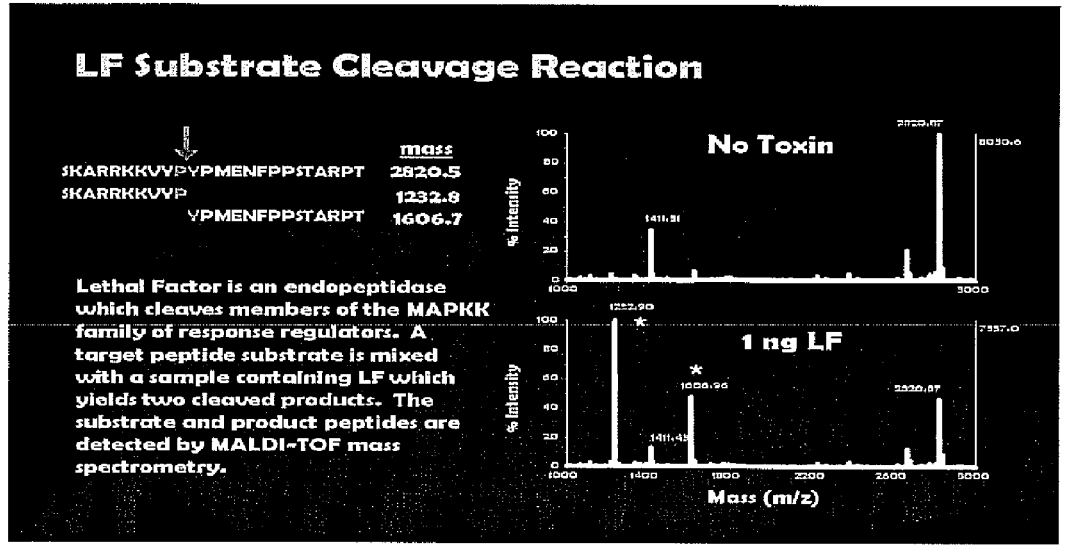
FIG. 2 is MALDI-TOF mass spectra of lethal factor specific cleavage of a peptide substrate, in which lethal factor (LF) coated MABs are incubated with 5 nmoles of synthetic peptide substrate SKARRKKVYPMENFPPSTARPT (Seq. No. 1) in 200 µl buffer over 2 hours at 37° C. to allow for cleavage product formation with the 2820.87 m/z of the substrate decreasing with cleavage and peaks of 1232.9 m/z and 1606.97 m/z corresponding to the N- and C-terminal cleavage products respectively appearing in the presence of LF-coated MABs.

Processes and substrates are provided to rapidly and reliably recognize infection by *B. anthracis* infection in an animal or human host. The present invention provides methods for rapidly isolating and concentrating LTx and its active component LF and then efficiently detecting the activity of LF as a marker of *B. anthracis* infection in a host.

By capitalizing on the enzymatic activity of the LF to cleave inventive peptide substrates suitable for rapid detection and quantitation in a hospital or laboratory setting, the present invention has utility as a diagnostic test which guides patient treatment of *B. anthracis*. The inventive test is rapid, highly sensitive and specific acute phase. The instant invention also has utility as a tool for screening specific compared to conventional *B. anthracis* testing lethal factor inhibitors and for monitoring infection an LF toxemia for vaccine candidate trials. The present invention has utility in monitoring LTx toxemia. The present invention affords a process to monitor onset, progression, and response to treatment kinetics of *B. anthracis* infection, including the effectiveness of anthrax therapeutics.

Monitoring disease progression in a patient population is essential to providing optimal treatment following infective exposure to *B. anthracis*. Often distinguishing an infection by *B. anthracis* from other flu-like or febrile illnesses is difficult, particularly in a setting where exposure to *B. anthracis* is rare or the threat of bioterrorism is low. Early detection and identification of *B. anthracis* exposure in a bioterrorism situation is a benefit in tracking the infection source. Currently employed diagnostic techniques for identifying *B. anthracis* infection are ineffective from 4 to 8 days post infection. The present inventive process employs several levels of specificity including specific immunoabsorbance of LF or LTx and substrates that are highly specific for LF. Thus, the present invention has the capability of detecting *B. anthracis* infection less than two days post exposure. It is appreciated that the present invention offers results within 4 hours of obtaining a biological sample such that directed treatment strategies may begin earlier and enhancing potential patient survival.

A biological sample is obtained from a patient or test subject and immediately sampled or alternatively frozen for later analysis at the situs of collection or remote from the source of the sample. A nonlimiting example includes samples taken in environments lacking state of the art diagnostic instruments. A simple blood sample is drawn into vacutainer or other tubes known in the art and then immediately frozen for prompt shipment. As a result, a diagnosis of infection is obtained in as little as 12-24 hours following a patient presenting symptoms of exposure to *B. anthracis*.

An inventive kit employs prepackaged anti-LF or anti-LTx coated beads to isolate LF from a biological sample. A reaction chamber is provided for isolation and purification. Buffers are optionally included with the kit to be illustratively used for washing the beads, diluting the biological sample, eluting the beads, reacting with the peptide substrate, reconstituting the peptide substrate, storing the beads, storing the peptide substrate, freezing or otherwise storing the isolated and concentrated LF, freezing or otherwise storing the cleavage products, or preparing samples for detection. Suitable buffers illustratively include phosphate buffered saline (PBS), phosphate buffered saline plus Tween-20 (PBS-T), HEPES buffered saline (HBS), HBS-Tween-20 (HBS-T), citrate-phosphate buffers, water, or other suitable buffers known in the art. The reaction chamber is used for cleavage of a peptide substrate. Optionally, a second reaction chamber is provided for cleavage of a peptide substrate. The isolated LF is appreciated to be amenable to freezing and shipment for remote analysis. It is further appreciated that cleavage products are also amenable to freezing for later detection, quantification or analysis at a remote location and time. These or other methods of employing the present invention may be used to deliver rapid, effective diagnosis on a worldwide scale in a time frame that is not possible with current diagnostic techniques.

It is appreciated in that that present invention is also applied to screening foodstuffs for human or other animal consumption. Wild animals or farm animals become infected by *B. anthracis* from food that is contaminated with the bacteria. People are commonly exposed to anthrax from contaminated animals or animal products. Biological samples from meat processing plants are rapidly screened for prior exposure to anthrax. It is appreciated that a biological sample illustratively includes whole blood, plasma, serum, extracellular fluid, cytosolic fluid, or tissue and other fluids known to harbor the bacteria. Simple techniques known in the art may be employed to homogenize, liquefy, or otherwise process the sample for analysis by the present invention. In instances when tissue is sampled, the sample is amenable to being frozen and analyzed remotely in time and place. Alternatively, an inventive field kit is employed.

Soil samples are also analyzed by the present inventive process for the presence of *B. anthracis*. Direct soil samples are used or "incubator" cells may be employed to provide a system by which exposure may be studied.

The inventive method is performed using numerous biological samples illustratively including whole blood, plasma, serum, extracellular fluid, cytosolic fluid, or tissue. Typically, serum is used as a suitable biological sample due to the ease in obtaining a sample by a venous blood draw from a patient or other test subject. It is recognized in the art that numerous other biological samples are suitable in the present invention dependent on the application desired. By way of example, a biological sample may be as simple as an aqueous buffering agent such as HBS or PBS, any of which are spiked with known or unknown levels of LF. Cell growth media is also suitable as a biological sample for screening transfected cell cultures for expression of active LF according to the present invention. It is appreciated that other biological samples are used such as a homogenized tissue sample that may or may not have been infected with anthrax.

Numerous biological species are suitable as sources of biological samples for use in the inventive methods. As used herein, a "host", synonymously described herein as a patient or subject, is any organism able to sustain *Bacillus anthracis* bacteria or produce LF and specifically includes nonhuman primates, such as monkeys, baboons, chimpanzees and gorillas; humans; ruminates such as sheep, cows and goats; and rabbits. The inventive process is also operative as a diagnostic tool to identify and monitor the progression of infection by anthrax spores such as may occur following a bioterrorist attack. However, it is recognized in the art that the invention is used in numerous other types of analyses illustratively including screening for suitable vaccines and for efficacy of therapeutics such as anthrax immune globulin (AIG) and anti-PA antibodies in an in vitro screening assay where the source of the LF may be transfected protein expressing cell lines. Another nonlimiting use is the screening of cattle that that have been found dead on a ranch such that the remainder of the herd may be rapidly and properly isolated from any infected animals reducing the impact of a disease outbreak.

Upon selection of a biological sample, detecting LF by the present inventive process involves isolating and concentrating LF in said biological sample. Preferably, nonporous magnetic beads coated with protein-G and reacted with antibodies that recognize and bind LF are employed to capture the LF from the biological sample. Magnetic beads have the advantage of requiring no centrifugation, thus allowing magnetic bead regeneration without loss of binding capacity. Magnetic beads also allow for minimal loss of sample due to pipetting as magnetic beads migrate to the sides of the reaction tube. It is further appreciated that magnetic beads allow for small scale isolation methods minimizing biological sample requirements. Other bead types or compositions operative herein illustratively include agarose, sepharose, nickel, or other materials known in the art. Numerous commercial sources are available for protein purification beads including New England Biolabs, Quiagen and Bachem.

Figure 1:
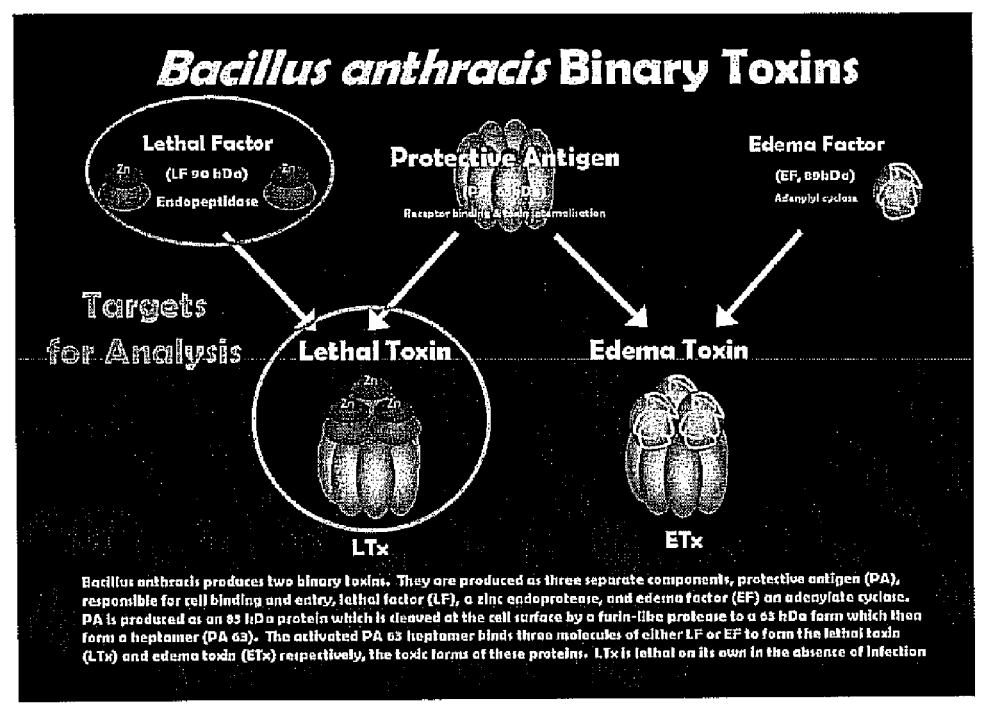

Protein-G coated magnetic beads suitable for use in the present inventive process are prepared and reacted with a suitable antibody for recognizing and binding LF. Monoclonal antibodies, polyclonal antibodies, or combinations thereof are suitable for selective LF binding. Preferably, monoclonal antibodies are used that recognize a region on LF that does not result in interference with the protease activity of the toxin. The antibodies are readily derived from numerous organisms including, but not limited to a human, mouse, rabbit, monkey, donkey, horse, rat, swine, cat, chicken, goat, guinea pig, hamster, or sheep. Antibodies specific for LF are readily obtained from numerous commercial sources including HyTest, Ltd; Santa Cruz Biotechnology; or Millipore. Preferably anti-LF antibodies derived from a rabbit or a macaque monkey are reacted with protein-G coated beads such that the antibodies are adsorbed to the beads. It is appreciated that antibodies directed to PA, LTx, EF, edema toxin, *B. anthracis* surface protein IsdC, *B. anthracis* sortase B, and extracellular excreted metalloproteinases produced by *B. anthracis* as detailed in A. I. Aronson et al., J. Biol. Chem. 187:3133-3138 (2005) are similarly employed in conjunction with, or as an alternative to LF. These antigen targets of antibodies are collectively defined as anthrax pathogenicity factor (APF). A schematic of *B. anthracis* APFs is provided in FIG. 1 with the exemplary LF and LTx couplet of toxins detailed in the following examples being highlighted. The beads are then blocked with bovine serum albumin (BSA), polyethylene glycol (PEG), or other blocking agents known in the art. A biological sample is incubated with the anti-APF coated beads for sufficient time to allow equilibrium binding to develop, generally between 1 minute and 3 hours depending on the affinity of the antibody and the anticipated concentration of APF in the biological sample. APF bound beads are then washed with a suitable buffer such as PBS-T, HBS-PEG, or other suitable buffering system known in the art to remove any unbound protein or other serum components. An appropriate APF peptide substrate is added to the washed beads and incubated between 1 minute and 20 hours, and typically about 1 hour. However, it is recognized in the art that the appropriate incubation time depends on substrate affinity, kinetic or catalytic efficiency constants intrinsic to the selected peptide substrate such that a detectable amount of product is formed in the incubation time. Such constants are readily determined by techniques well known and commonly practiced in the art.

Peptide substrates operative in the present inventive process are selected based on known affinity and kinetic constants as well as by the method of detection to be employed under the inventive method. Preferably, a peptide substrate possesses one potential scissile bond to simplify the kinetics of the cleavage reaction. The selected peptide substrate mimics the natural target of APF or is a natural target of APF depending on the assay detection method to be employed. Typically the selected peptide is comprised of between 2 and 100 amino acid residues and preferably contains more than 10 residues. Preferably, the present invention is practiced with peptide substrates that mimic the sequence of the regions surrounding the scissile bond in natural LF target proteins. However, it is appreciated that other amino acid residues are optionally substituted within the sequence. For example, one or more amino acid residues within a sequence can be substituted by another amino acid of a similar polarity which acts as a functional equivalent. Substitutes for an amino acid within the sequence are illustratively selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the present invention are ligands or fragments or derivatives thereof which are differentially modified during or after translation, e.g., by glycosylation, phosphorylation, acetylation, sulfation, linkage to an antibody molecule, or other cellular ligands.

It is also appreciated that an appropriate substitution is optionally employed that increases the catalytic efficiency of the cleavage reaction. A nonlimiting illustration includes the substation of alanine for isolucine at the P1' position that results in a nearly 9-fold increase in catalytic efficiency. (Turk, B. E. et al. (2004), *Nature Struc. Mol. Biol.,* 11:60-66). A percent homology of greater than 50% is required and preferably greater than 90%. The percent homology is calculated by standard methods Current Methods in Sequence Comparison and Analysis," *Macromolecule* Sequencing and Synthesis, Selected Methods and Applications, pp. 127-149, 1998, Alan R. Liss, Inc. Numerous other peptide sequences are known in the art. Representative peptides sequences operative in the present invention include:

SKARRKKVYPMENFPPSTARPT; (Seq. No. 1)

RRKKVYPYPMETIA; (Seq. No. 2)

RRKKVYPYPMETIAK; (Seq. No. 3)

SPARRKKVYPYPMENPTPRSTPSPT; (Seq. No. 4)

SKARRKKVYPYPMENFPPSTARPT; (Seq. No. 5)

(Nle)KKKKVLPIQLNAATD; (Seq. No. 6)

(Flu)MPKKKPTPIQLNPAPD-NH2; (Seq. No. 7)

(Flu)NlePKKKPTPIQLNPAPDKGG-NH2; (Seq. No. 8)

(Flu)NleKKKKVLPIQLNAATDKGG-NH2; (Seq. No. 9)

(Cou)NleKKKKVLPIQLNAATDK(QSY-35)GG-NH2; (Seq. No. 10)

(Cou)NleKKKKVLPTQLNAATDK(DAB)GG-NH2; (Seq. No. 11)

(QSY-35)NleKKKKVLPIQLNAATDK(Cou)GG-NH2; (Seq. No. 12)

(DAB)NleKKKKVLPIQLNAATDK(Cou)GG-NH2; (Seq. No, 13)

RRKKVYPYPMEPTIA; (Seq. No. 14)

SKARRKKVYPYPXENFPPSTARPT; (Seq. No. 15)
(X = norleucine)

(MCA)-SKARRKKVYPYPXENFPPSTAR-(DNP); (Seq. No. 16)
(X = norleucine)

(oAbz)-SKARRKKVYPYPXENFPPSTAR-(DNP); (Seq. No. 17)
(X = norleucine)
and

SKARRKKVYPYPMENFPPSTARPT(FTIC-DABACYL); (Seq. No. 18)

where Flu: 5,6-carboxyfluresceinyl; FTIC: fluorophore-thiocarbamoyl; Cou: 7-hydroxy-4-methyl-3-acetylcoumarinyl; DAB: 4-dimethylaminoazobenzene-4'-carboxyl; and QSY-35, N-({4-[(7-nitro-2,1,3-benzoxadiazol-4-yl)amino]phenyl}acetyl. It is appreciated in the art that numerous other peptide sequences are similarly employed. It is also appreciated in the art that the presence or absence of optically active molecular groups may be added to positions within a peptide sequence should detection by fluorescence or optical density be desired. Such optical moieties illustratively include pNA (p-nitroaniline) and AMC (amino-methyl coumarin).

Alternatively, the peptide substrate is tagged with a biotin, avidin, horseradish peroxidase, streptavidin, or digoxin molecule. A nonlimiting example illustratively includes the addition of biotin to a residue within the peptide substrate such that upon cleavage a peptide of reduced size retains the biotin molecule(s) that is subsequently purified on an avidin column for further characterization or quantitation.

In a preferred embodiment a peptide substrate contains multiple molecular modifications such as a coumarin fluorophore (7-hydroxy-4-methyl-3-acetylcoumarinyl; $\lambda_{ex}$ 386 nm, $\lambda_{em}$ 448 nm) paired with either 4-dimethylaminoazobenzene-4'-carboxyl (DABCYL; $\lambda_{max}$ 454 nm) or QSY-35 [(N-({4-[(7-nitro-2,1,3-benzoxadiazol-4-yl)amino]phenyl}-acetyl), $\lambda_{max}$ 475 nm] as the quencher. Thus, a FRET based assay is available with little background fluorescence due to a FRET in the intact substrate between the fluorophore and the quencher that prevents light emission in the uncleaved peptide substrate. When the substrate is cleaved by APF and preferably LF, an increase in fluorescent light emission by the coumarin fluorophore is readily detected with a bench-top fluorometer.

Alternatively, a substrate undergoes a colorimetric reaction. For example a substrate containing a p-nitroaniline or other group known in the art results in a color change in the solution following substrate cleavage by APF such as LF. The creation of a species that modifies solution pH is also discernable through colorimetric monitoring of a pH indicator, or use of an ion selective electrode. Such a colorimetric assay can be performed either continuously or discontinuously and is further amenable to plate based assay formats similar to the FRET based or other fluorescence assays described above.

The present inventive method is amenable to numerous detection protocols and apparatus. In a preferred embodiment a sample of the analyte is analyzed by MALDI-TOF. MALDI-TOF has the advantage of recognizing particular cleavage products by resulting peptide masses. Comparison with an internal standard fixes the cleavage product mass. Internal standards illustratively include adrenocorticotropic hormone (ACTH), bradykinin, and angiotensin II. In a preferred embodiment an internal standard is an isotopically labeled peptide seven mass units higher than and corresponding to the sequence of the target cleavage peptide. Using a ratio of the area under the peak representing the target peptide and that representing the internal standard a relative quantity of the target peptide is obtained. Exemplary MALDI-TOF spectra absent toxin and with 1 nanogram (ng) LF are shown in the presence of a standard at mass (m/z) of about 1411 are provided in FIG. 2. Analyses of samples at numerous time points following addition of the peptide substrate to the reaction chamber allows for kinetic measurements of product formation and determination of the amount of APF present in the original biological sample. It is recognized in the art that numerous other forms of mass spectrometry may be employed as detection methods in the present invention such as electro-spray ionization LC/MS/MS, etc.

In another preferred embodiment detection of cleavage products is performed using a simple bench-top fluorometer. Employing dual labeled peptide substrate with a fluorescent group placed either N- or C-terminal to the scissile bond and a quenching group placed an appropriate distance from the fluorescent group on the opposite end of the scissile bond allows for rapid and real-time monitoring of reaction product formation following cleavage of the substrate reducing the FRET and resulting in an increase in observable fluorescence, as shown in FIG. 11. Optionally, the reaction is quenched by the addition of 1 mM ortho-phenanthroline/10 mM EDTA after a known amount of time has elapsed following substrate addition to the reaction chamber. The magnitude of the fluorescence is measured and compared to a standard curve for determination of product formation per unit time that is then related back to the unknown activity of APF in the reaction. The endpoint analysis is particularly amenable to being performed in 96-well plate format for robotic processing and improving screening throughput. It is recognized in the art that both continuous and endpoint assay and detection methods are amenable to miniaturization to 384 well, 1096 well, or other plate based assay formats.

Screening APF inhibitors in vivo provides physiologically relevant information as to the potency, bioavailability, rate of clearance, and efficacy of potential small molecule or antibody based inhibitors of APF. The present invention is particularly useful as a rapid, high-throughput assay format for screening such inhibitors. The detection limit using MALDI-TOF analysis is as low as 5 picograms (pg) of specific LF activity and comparable for other APF on a mole basis The assay successfully detects 59 pg of specific LF activity in as little as 5 µl of sera from host with inhalation anthrax. Antibodies are available or are raised against APF from numerous species commonly used for screening purposes such as murine, rabbit, guinea pig, hamster, canine, swine, or monkey. Techniques for raising antibodies to molecular targets are well known in the art. A nonlimiting example is early in vivo screening protocols employing mice who are dosed with small molecule or other compounds. The mouse is optionally subjected to inhalation anthrax or other forms to initiate an onset of infection. Following administration of a lead compound directed toward preventing anthrax infection, proliferation, ability of toxins to bind to target cells, or other mechanisms of anthrax infection, small blood samples are acquired and analyzed by the present invention for LF activity. As the present invention requires only modest serum quantities such as 5 μl, numerous time points are readily obtained from a single mouse allowing for in vivo kinetic measurements.

The present invention is also employed in screening protocols for the identification and trials of candidate vaccines by allowing rapid observation of the degree to which antibodies generated by a vaccine neutralize catalytic activity associated with a given APF.

As the present invention capitalizes on the activity of APF in a biological sample, it is operative to predict the disease progression in animals that have been subjected to anthrax infection that may or may not have been pretreated with a vaccine candidate. A correlation is expected between the efficacy of a vaccine and reduced levels of APF present in a biological sample from a test host. As such, sampling host tissues or fluid samples following the initiation of infection provides a real-time readout of the progress of the infection. A reduction of the levels of APF activity in a host treated with a vaccine serves as a direct measure of vaccine efficacy. Thus, the present invention has numerous advantages over simple death screening models as it is expected to provide a superior correlation with lower levels of vaccine efficacy providing investigators with data that allows for more complete differentiation between possible candidate vaccines. It is further appreciated that numerous additional parameters of protection may be analyzed using the present invention. The present invention is well suited to determine alterations in the rate of infection progression, levels of free LF, levels of LTx, other APFs, rate of disease resolution, or other parameters common to the art to screen, differentiate, or monitor vaccine performance.

While the present invention detects 5 picograms (pg) of LF in a sample of 5 microliters (μl), it is appreciated that the subject invention is readily practiced with a larger sample toxin quantity, volume, or both. The ability of specific antibodies coated on beads may be used to isolate LF, LTx, or other APFs in large sample volumes such as from wet soil by simple agitation of the sample such that the beads remain in suspension for the isolation period. In this way even dilute biological samples may be screened for the presence of anthrax.

Optionally, the present inventive method is used to isolate and identify other proteases with specific substrates and is not limited to APFs. The present invention has utility as a diagnostic for a variety of disease conditions or deficiencies. These conditions and deficiencies illustratively include: hepatitis, enzyme deficiency, erythropoietin, catalase, endotoxic shock/sepsis, adenosine deaminase for treatment of severe combined immunodeficiency, lipid-binding protein (LBP), purine nucleotide phosphorylase, galactosidase, beta-glucuronidase, antioxidants for cancer, therapy anemia, superoxide dismutase, cancer, growth factors for use in wound healing, induction of red blood cell formation and the like, α-interferon, β-interferon, epidermal growth factor, granulocyte colony stimulating factor (G-CSF), alpha-IL1, gamma-interferon, phenylalanine ammonia lyase, transforming growth factor, arginase, erythropoietin, L-asparaginase, thrombopoietin, uricase, insulin-like growth factor-1, insulin, human growth hormone, monoclonal antibodies, tissue necrosis factor, cardiovascular disease, diabetes, tissue plasminogen activator, urokinase (native or chimeric), glucagon, α1-antitrypsin, insulinotrophic hormone, clotting disorders, antithrombin-III, other proteases or protease inhibitors, coagulation factors Xa, VIIa, XIa, XIIa, IXa, thrombin, the presence or absence of cofactor clotting factors VIII, V or others, apolipoproteins (particularly B-48), circulating scavenger receptor, APO A1 which converts low-density lipoproteins to high-density lipoproteins, gastrointestinal and pancreatic deficiencies, obesity and feeding, pepsin (for esophageal reflux), Ob gene product, cholecystokinin (CCK), trypsin, chymotrypsin, bone diseases, elastase, carboxypeptidase, calcitonin, lactase (for lactose deficiency), PTH-like hormone, sucrase, intrinsic factor (pernicious anemia), myasthenia gravis (acetylcholine receptors), Graves' disease (thyroid-stimulating hormone receptor), organ-specific autoimmune diseases (target of antibody in parentheses), thyroiditis (thyroid, peroxidase), insulin-resistant diabetes with acanthosis nigricans or with ataxia telangiectasia (insulin receptor), allergic rhinitis, asthma (β2-adrenergic receptors), juvenile insulin-dependent diabetes (insulin, GAD65), pernicious anemia (gastric parietal cells, vitamin B12 binding site of intrinsic factor), Addison's disease (adrenal cells), idiopathic hypoparathyroidism (parathyroid cells), spontaneous infertility (sperm), premature ovarian failure (interstitial cells, corpus luteum cells), pemphigus (intercellular substance of skin and mucosa), bullous pemphigoid (basement membrane zone of skin and mucosa), primary biliary cirrhosis (mitochondria), autoimmune hemolytic anemia (erythrocytes), idiopathic thrombocytopenic purpura (platelet), idiopathic neutropenia (neutrophils), vitiligo (melanocytes), osteosclerosis and Meniere's disease (type II collagen), chronic active hepatitis (nuclei of hepatocytes), systemic autoimmune diseases (defect/organ affected in parentheses), Goodpasture's syndrome (basement membranes), rheumatoid arthritis (γ-globulin, EBV-related antigens, collagen types II and III), Sjogren's syndrome (γ-globulin, SS-A (Ro), SS-B (La), systemic lupus erythematosus (nuclei, double-stranded DNA, single-stranded DNA, Sm ribonucleoprotein, lymphocytes, erythrocytes, neurons, gamma-globulin), scleroderm (nuclei, Scl-70, SS-A (Ro), SS-B (La), centromere, polymyositis (nuclei, Jo-1, PL-7, histadyl-tRNA synthetase, threonyl-tRNA synthetase, PM-1, Mi-2), rheumatic fever (myocardium heart valves), and choroid plexus.

The present invention is further detailed with respect to LF and LTx purification and detection as representative of the present invention detection of other enzymatic APFs and other disease associated proteases. The following examples are not intended to limit the scope of the claimed invention and instead provide specific working embodiments.

EXAMPLES

Example 1

Preparation of Protein G Beads

Protein G coated beads are obtained from Invitrogen. 20-100 µl of bead suspension are used to covalently link Ig from a 100 µl sample to the beads according to the manufacturers protocol. To separate the beads the reaction tube is placed on a magnet for 1 min and the resulting supernatant discarded by aspiration. The beads are resuspended in phosphate buffered saline with 0.05% Tween20, pH 7.3 (PBS-TW) and stored until ready for use Thorough washing is achieved by repeating the magnetic pelleting and resuspension steps three times.

Example 2

Coating Protein G Beads with Desired Anti-LF Antibody

Anti-LF coated magnetic beads (LF-MABs) are prepared using mouse monoclonal anti-LF IgG that is prepared according to the manufacturer's protocol (Invitrogen) using 40 ug IgG/100 ul magnetic bead suspension.

Example 3

Purification and Concentration of LF from Serum

Figure 3C:
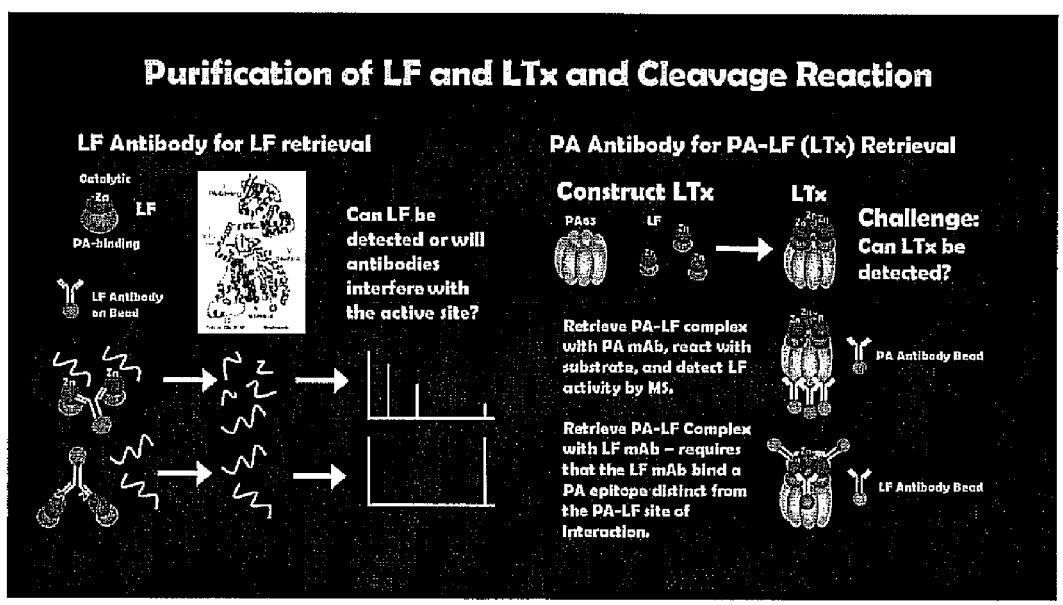
FIG. 3C is a schematic depiction of isolation and purification of LF and *B. anthracis* lethal toxin (LTx).
Figure 3A:
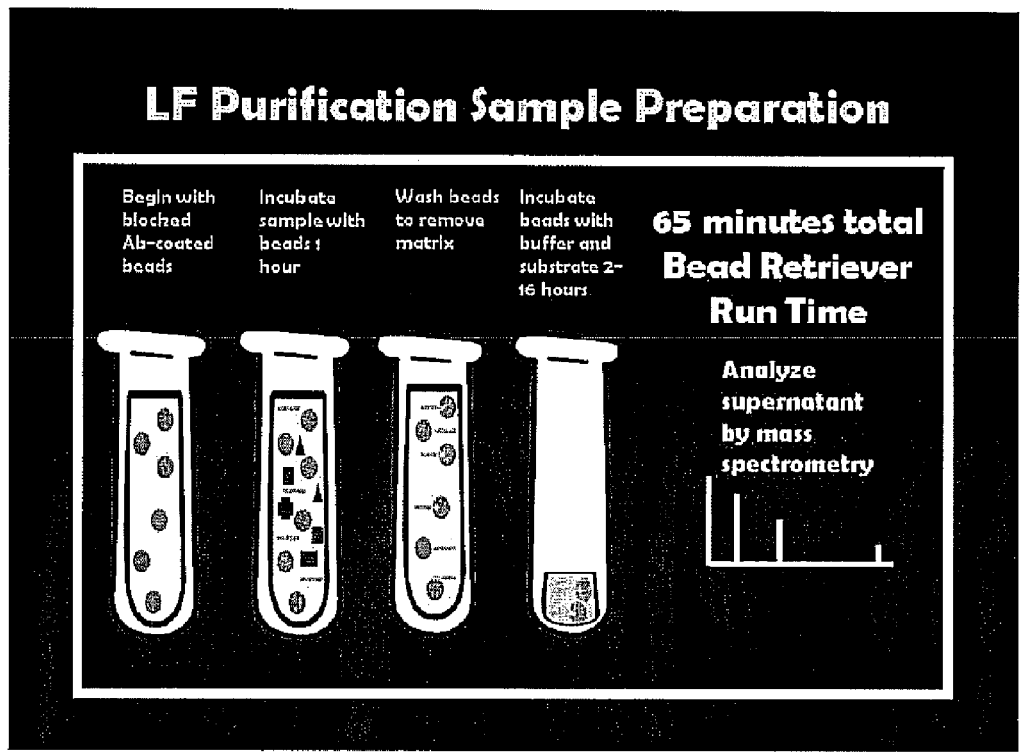
FIG. 3A is a schematic of a protocol for isolation and concentration of LF from a biological sample.
Figure 3B:
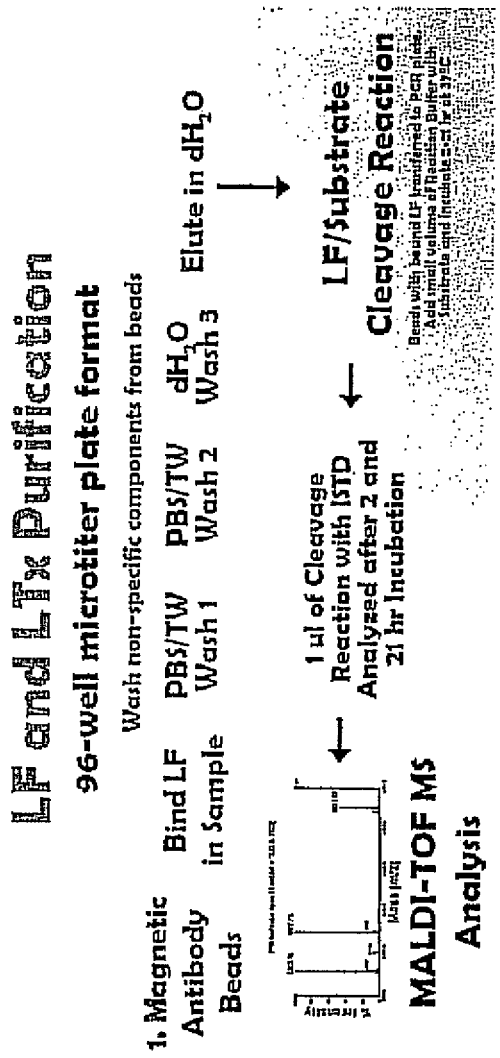
FIG. 3B is a process schematic depicting isolation and concentration coupled to the enzymatic cleavage of a peptide substrate of which the cleavage products are analyzed by MALDI-TOF.

A serum, plasma, pleural fluid or other biological sample is obtained from a patient or infected animal. The sample is diluted in 500 µl PBS-TW and mixed gently with 20 µl MAB-sLF MABs for 1 hour. The beads with LF and LTx bound are retrieved, washed three times in PBS-TW, then reconstituted in PBS-TW for further analyses by mass spectrometry, as shown in FIGS. 3A and 3B.

Example 4

On-Bead Substrate Cleavage Reaction

LF-coated MABsMABs are incubated with 5 nmoles of synthetic peptide substrate SKARRKKVYPMENFPP-STARPT (Seq. No. 1) in 200 µl buffer over 2 hours at 37° C. to allow for cleavage product formation. Samples of the cleavage reaction are taken at times 5, 10, 15, 30, 45, 60, 90, 120, and 240 minutes, LF-bound MABs in each sample are pelleted by magnetic separation and a small fraction (1 µl) of the cleavage product containing supernatant are removed for subsequent MS identification and quantitation, as shown in FIG. 3A.

Example 5

LF and LTx Purification

The purification of LF and LTx in a 96-well microtiter plate format is provided in FIG. 3B in which magnetic antibody beads are provided as detailed in Example 2 and bind LF from a sample per Example 3. The beads with LF bound are washed twice in PBS-TW per Example 2 with a final wash in deionized water. LF is then eluted in deionized water and beads with bound LF are transferred to the polymerase chain reaction (PCR) plate and incubated in 40 µl buffer for between 2 and 21 hours at 37° C. to allow the cleavage reaction to proceed. 1 µl of cleavage reaction dilution with a proteinaceous internal standard is analyzed after 2 hours and 21 hours of incubation by MALDI-TOF mass spectrometry. LF is detectable in this manner, indicating that anti-LF antibodies do not interfere with the active site for the cleavage reaction in LF. In the event that interference were to occur, the mass spectrum as detailed in the lower left-hand corner of FIG. 3C is anticipated. Non-interference by the antibody was predicted to provide a mass spectrum showing a depletion of cleavage substrate and intensity increase for masses associated with cleavage fragments, as shown in the left middle portion of FIG. 3C.

Protective antigen antibody for LTx retrieval begins with PA mAb that is specific for the distal portion of PA63 kilodalton as depicted in FIG. 1 where the antibody bonds to PA63 remote from the PA lethal factor (LTx) interface. The PA mAb bound LTx is then reacted with a proteinaceous substrate or lethal factor where lethal factor enzymatic activity is detected by mass spectrometry, as shown in FIG. 3C, right middle. An attempt to retrieve LTx with LF mAb requires that the LF mAb bind a protective antigen epitope distinct from the interaction interface between the protective antigen and lethal factor exposing LTx bound to LF antibody to a proteinaceous substrate for LF and allows for detection of LF enzymatic activity by mass spectrometry, as shown in FIG. 3C, lower right, to determine the efficacy of the present invention to detect LTx.

Example 6

Comparison of Peptide Substrates

Four substrate peptides are compared for potential use in an inventive process. FIGS. 4A-D represent mass spectra of four different substrates (LF1-1-RRKKVYPYPMEPTIA (Seq ID. No. 14); LF-2 RRKKVYPYPMEPTIAK (Seq ID. No. 3); LF-3 SPARRKKVYPYPMENPTPRSTPSPT (Seq ID. No. 4); LF-4 SKARRKKVYPYPMENFPP-STARPT (Seq ID. No. 5). FIG. 4A shows the mass spectrum for LF-1 that is based on a FRET substrate optimized RET substrate optimized by Turk et al. (2004), *Nat. Struc. Mol. Biol.,* 11:60-66); LF-2 includes one additional lysine on the carboxy-terminus; FIG. 4B is a mass spectrum for substrate LF-2 that includes one additional lysine on the carboxy-terminus; FIGS. 4C and 4D are mass spectra for substrates LF-3 and LF-4 respectively that include 10 additional amino acids based on the extended consensus sequence of MAPKK. For these reactions 10 ng LF is incubated with 5 nmoles of each substrate in 200 µl buffer for 2 hours at 37° C., sampled at times 5, 10, 15, 30, 45, 60, 90, 120, and 240 minutes for MALDI-TOF analysis with relative quantification. At 120 minutes, 1 µl of each reaction is analyzed without ISTD peptides to acquire the spectra shown in FIGS. 4A-D. FIG. 4E is a plot of the area ratio of the peaks for the amino terminal product peptides of FIGS. 4A-4B relative to an ISTD peptide over time giving the relative rates of reaction for each peptide.

Figure 5:
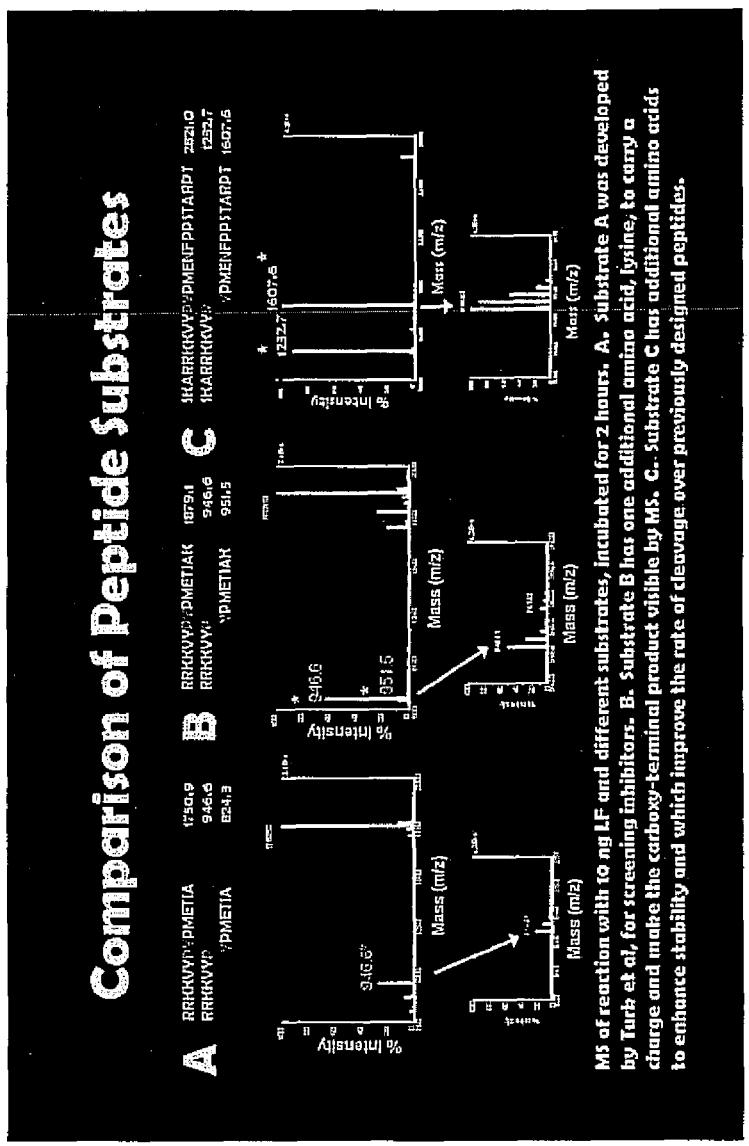
FIG. 5 is mass spectra plots of relative catalytic efficiency of cleavage for peptide substrates Seq. Nos. 1-3.

FIGS. 5A-C reproduce the spectra of FIGS. 4A, 4B and 4D, respectively, and also provide a magnified region of the mass spectra in the region surrounding proteinaceous cleavage products having molecular weight weighted averages of 946.6, 946.6, and 1232.7, respectively.

Example 7

Purification of LF and LTx with LF MABs and LTx with PA MABs 500 pg of LF are retrieved with LF MABs without affecting the ability of LF to enzymatically cleave substrate LF-4 in FIG. 4D, as demonstrated in FIG. 6A. A like amount of LF (500 pg) complexed with PA (PA-LF or LTx) is also retrieved with LF MABs then mixed with buffer and substrate peptide LF-4 and incubated for 16 hours at 37° C. consistent with the procedures detailed in the above examples to obtain the mass spectrum of FIG. 6B. LTx containing 500 pg of LF is retrieved with PA MABsMABs consistent with the above examples followed by mixing with buffer and LF-4 substrate peptide and incubated for 16 hours at 37° C. to obtain the mass spectrum of FIG. 6A. The spectra of FIGS. 6A-C confirm the ability to purify LF with LF MABs and LTx with either LF MABs or PA MABs. These spectra establish that more substrate is consumed and more cleavage product peptide produced by LTx bound by PA MABs relative to LF MABs.

Example 8

Off-Bead Substrate Cleavage Reaction

LF or LF-PA are isolated from a patient serum sample by incubation with MABs for 40 min. LF-bound MABs are then washed twice in PBS-T and once in dH$_2$O to remove any unbound LF and serum components. For these reactions 10 ng LF is incubated with 5 nmoles of synthetic peptide substrate SKARRKKVYPMENFPPSTARPT (Seq. No. 1) in 200 µl buffer over 2 hours at 37° C., and sampled at times 5, 10, 15, 30, 45, 60, 90, 120, and 240 minutes. A small fraction of the cleavage product is removed for subsequent MS identification and quantitation.

Example 9

Identification of Cleavage Products by MALDI-TOF Mass Spectrometry

A small fraction (1 µl) of the peptide substrate cleavage reaction solution is removed and mixed with an internal standard (ITSD). An ionization matrix such as α-Cyano-4-hydroxycinnamic acid (CHCA) is added and the sample spotted on a MALDI-TOF plate in triplicate. The spectra is obtained in positive-ion mode with delayed extraction on a suitable mass spectrometer such as a Voyager DE-Pro mass spectrometer (Perceptive Biosystems, Framingham, Mass.) equipped with a 337-nm nitrogen laser and a single-stage reflector. In this case, mass spectra were collected from 750 to 3200 mass/charge (m/z), in MS positive ion reflectron mode on the Applied Biosystems 4700 and 4800 Proteomics Analyzers (Framingham, Mass.). These instruments use a nitrogen laser at 337 nm and each final mass spectrum was an average of 2400 laser shots. As the sequence and mass of the peptide substrate are known, the cleavage products are readily identified.

Example 10

Comparison of LF Antibodies for LF Cleavage Assay

Figures 7, 8:
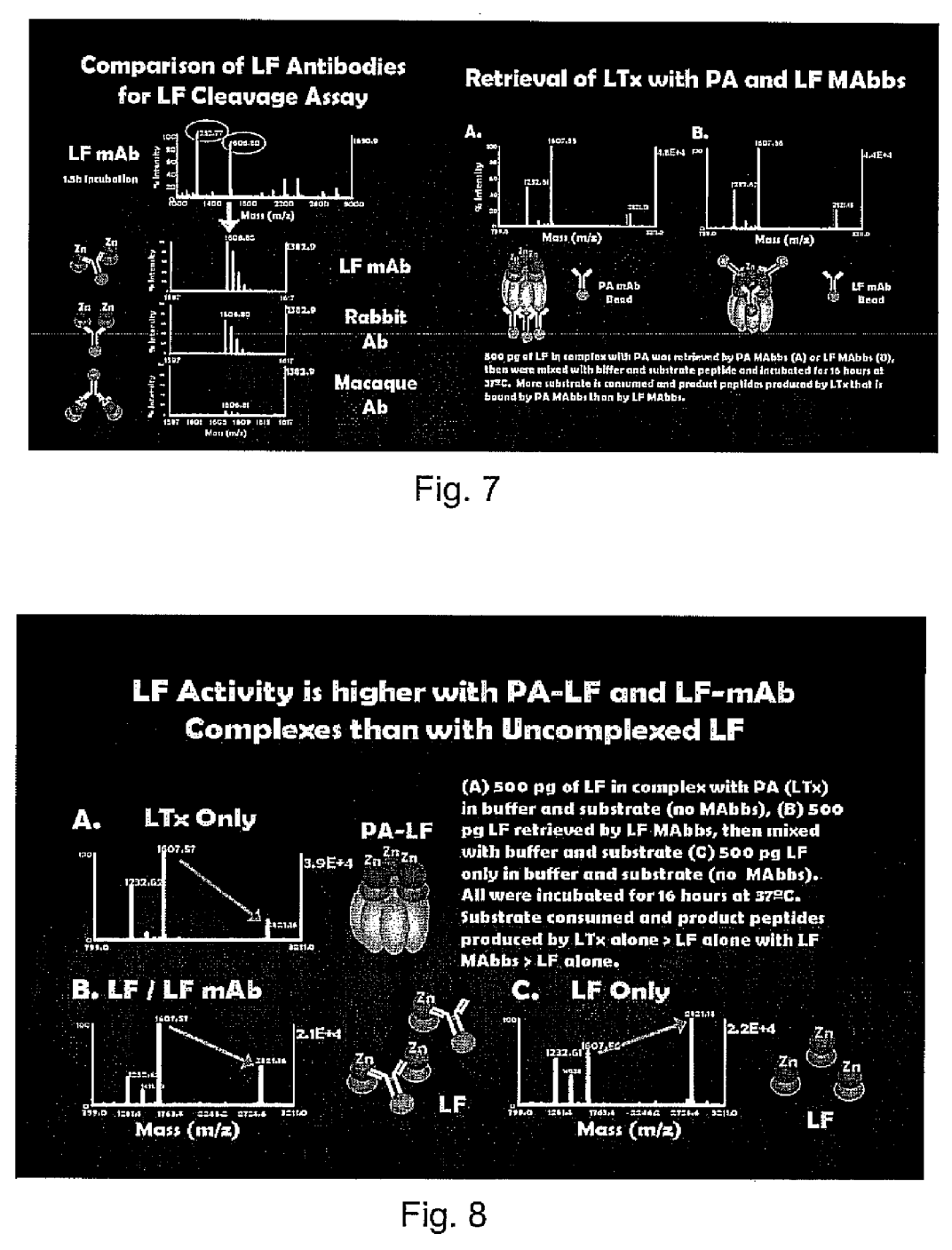

The procedure of Examples 2 and 3 is repeated with polyclonal rabbit and macaque antibody as shown in the left panel mass spectra of FIG. 7. Magnetic antibody beads are prepared from serum of rabbit and macaques immunized with recombinant LF. These are compared to the LF MABs with the mouse monoclonal LF antibodies bound. The results show that the mouse monoclonal targets a single epitope that does not interfere with catalytic activity of LF since it can still easily cleave the peptide substrate as evident from the large product peptide at 1607.8 m/z. The rabbit polyclonal which has many antibodies to several epitopes also does not interfere with the catalytic activity although the cleaved product peak intensity is less than that using the LF MABs. Conversely, the macaque antibodies significantly neutralize the catalytic activity of LF; very little substrate is cleaved and peptide products peaks have a reduced intensity.

Example 11

Determination of LF Activity in Uncomplexed and Antibody Bound Complex Forms To determine activity, 500 pg of LF in complex with PA (PA-LF or LTx) is placed in buffer and with no MABs peptide substrate LF-4 per FIG. 4D and incubated for 16 hours at 37° C. with the resulting mass spectra being depicted in FIG. 8A. This experiment is repeated with 500 pg of LF retrieved by LF MABs and mixed with buffer and substrate LF-4 in amounts as detailed above and incubated again at 16 hours at 37° C. with the resulting mass spectrum shown in FIG. 8B. This experiment is again repeated with 500 pg LF only in buffer and incubated for 16 hours at 37° C. with LF-4 peptide substrate (no MABs) with the resulting mass spectrum shown in FIG. 8C. FIGS. 8A-C indicate that under like conditions and in the presence of the same peptide substrate, LTx alone had greater activity than the LF retrieved from LF MABs which in turn had greater activity than LF alone.

Example 12

Quantitation of Cleavage Products by MALDI-TOF Mass Spectrometry

Figure 6:
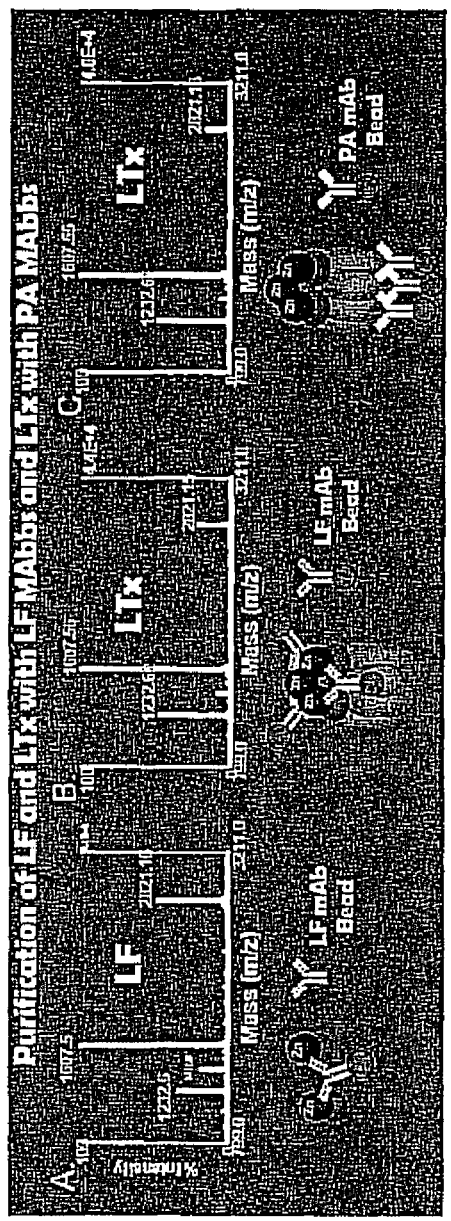
FIG. 6A is a mass spectrum and schematic structure for LF in the presence of LF mAB bead.
FIG. 6B is a mass spectrum and schematic structure for LF-PA (LTx) in the presence of LF mAb bead.
FIG. 6C is a mass spectrum and schematic structure for LTx in the presence of a PA specific maB.
Figure 9F:
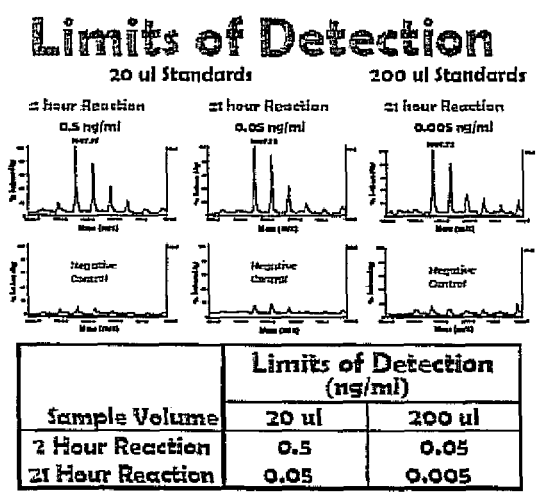
FIG. 9F is a series of mass spectra as a function of reaction time, concentration and standard quantity to provide detection limits; negative control spectra are also provided.

The mass spectrum of the LF cleavage reaction is provided in FIG. 9A for a procedure detailed with respect to FIG. 6. The desired cleavage product (mass 1607 m/z) is quantitated by ratio comparison to an isotopically labeled peptide of 7 mass units higher than the target at 1614 m/z that will be added as an ITSD to normalize spot to spot signal intensity differences. FIG. 9B shows magnified mass regions of the spectrum showing isotopic distribution. The spectra from three spots from one sample are shown in FIG. 9C indicating the varied intensity differences. The area of the isotopic peaks for the 1607 m/z LF-specific "target" (cleavage peptide) analyte divided by the area isotopic peaks of the labeled ISTD gives the area ratio which allows absolute quantitation when plotted vs. concentration and "normalizes" the spot to spot area differences as shown in FIG. 9D. A plot of the $\log_{10}$ of LF in ng/ml versus the $\log_{10}$ of the area ratio is plotted, as shown in FIG. 9E. A sigmoidal fit and interpolation allows calculation of the concentration of cleavage peptide present. A standard curve is constructed by plotting the amount of LF (pg) versus the area ratio. Unknowns are calculated from the slope. Detection limits at 2 and 21 hours incubation, 20 µl LF, and 200 µl LF with an incubation time for 21 hours is summarized in FIG. 9F.

Example 13

Identification and Quantitation of LF by Fluorescence Spectroscopy

Alternatively a peptide substrate that contains a fluorophore and a quenching molecule on opposing sides of the scissile bond will be employed to allow for detection of an increase in fluorescence following cleavage by LF or LTx. 25 μl of a 6 μM solution of peptide substrate (Cou)NleKKKKV-LPIQLNAATDK(QSY-35)GG-NH$_2$ (Seq. No. 10) in assay buffer will be added to 30 μl of the isolated and concentrated LF or LTx obtained from a biological sample as described. (Cummings R. T. et al. (2002), *PNAS USA*, 99:6603-6606). The cleavage reaction will be allowed to proceed for 2 hours and terminated at room temperature by the addition of 25 μl of 4 mM ortho-phenanthroline/40 mM EDTA. The resulting fluorescence will be read on an appropriate fluorometer (excitation 355 nm, emission 460 nm). The fluorescence value will be compared to a standard curve to determine the level of LF activity per unit reaction time.

Optionally, a continuous assay protocol will be performed to identify and quantitate LF or LTx isolated from a biological sample. A reaction tube comprised of 25 μl of a 6 μM solution of peptide substrate (Cou)NleKKKKVLPIQLNAATDK (QSY-35)GG-NH$_2$ (Seq. No. 10) in assay buffer will be added to 30 μl of the isolated and concentrated LF or LTx obtained from a biological sample and the reaction monitored continuously for 2 hours on an appropriate plate based fluorometer (excitation 355 nm, emission 460 nm). A standard curve comprised of increasing known quantities of LF or LTx will be present on the same plate and read simultaneously as the unknown samples. The rate of fluoresce increase of each unknown sample will be compared to the standard curve to determine the amount of LF activity present.

Example 14

Figures 10, 11A:
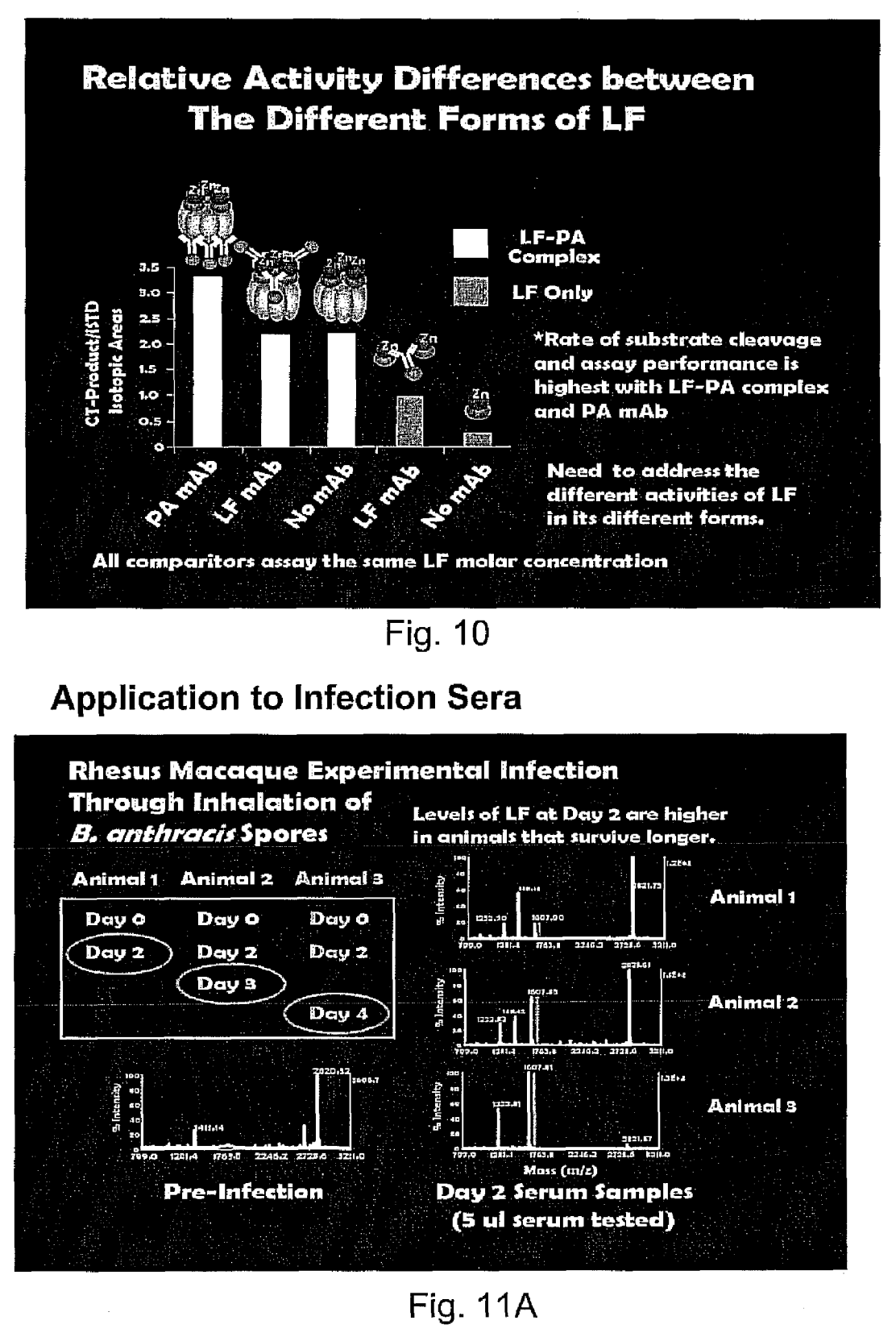

Rhesus Macaque Experimental Infection through Inhalation of *B. anthracis* Spores Three rhesus macaques are exposed to experimental infection using airborne spores of *B. anthracis* and monitored for onset of inhalation infection, rate of infection progression, and correlation with physiological complications. Biological samples of blood serum (5 μl) are taken from each animal prior to exposure to anthrax spores. Mass spectra of control reactions by the present inventive method demonstrate no observable background cleavage product at time zero as shown in FIG. 11A, lower left panel. Each animal is monitored and biological samples of serum are obtained each day. Each biological sample is assayed by the present inventive method for cleavage of synthetic peptide substrate SKAR-RKKVYPMENFPPSTARPT (Seq. No. 1) (m/z=2820.5). Cleavage products are identified and quantitated by MALDI-TOF mass spectrometry. At day 2 significant levels of LF are present in the biological samples as demonstrated by increasing levels of cleavage products at m/z=1232.8 and m/z=1606.7 as shown in FIG. 11A, right panel. The larger fragment will be used for quantitative purposes by the inclusion of and ISTD seven mass units higher than the target (m/z=1614). Levels of LF at day 2 are higher in animals that demonstrate increased survival time. Animal 1 shows the shortest time to mortality which correlates with the lowest level of LF activity. Animal 3 shows the longest time to mortality with a correspondingly high level of serum LF activity.

Figures 11B, 11C:
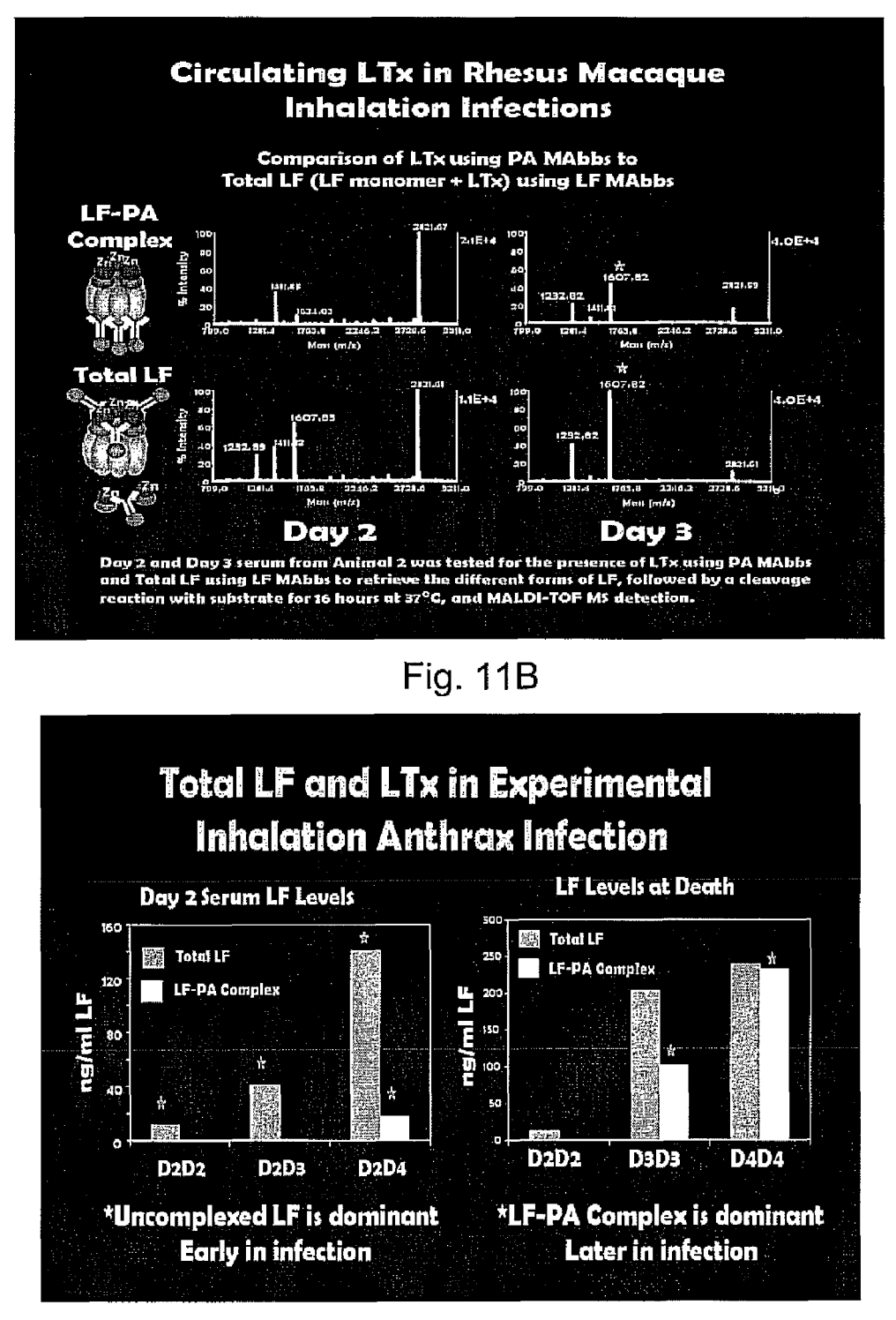

The inventive method is used to determine levels of LTx in rhesus macaque following a similar inhalation mediated infection by *B. anthracis*. Beads coated with MABs specific for PA that neither interfere with the interaction of PA with LF nor interfere with the catalytic activity of LF with respect to the target synthetic peptide substrates are employed. Comparisons between the levels of free LF and LTx are simultaneously obtained with the same biological sample at days 2 and 3 are shown in FIG. 11B. The levels of free LF will be lower earlier in the infection cycle. At death, the levels of LTx increase greater than 10-fold and are present at nearly equal molar levels to free LF indicating that severe toxemia is proportional to increased relative levels of LTx as shown in FIG. 11C.

Example 15

Figure 12:
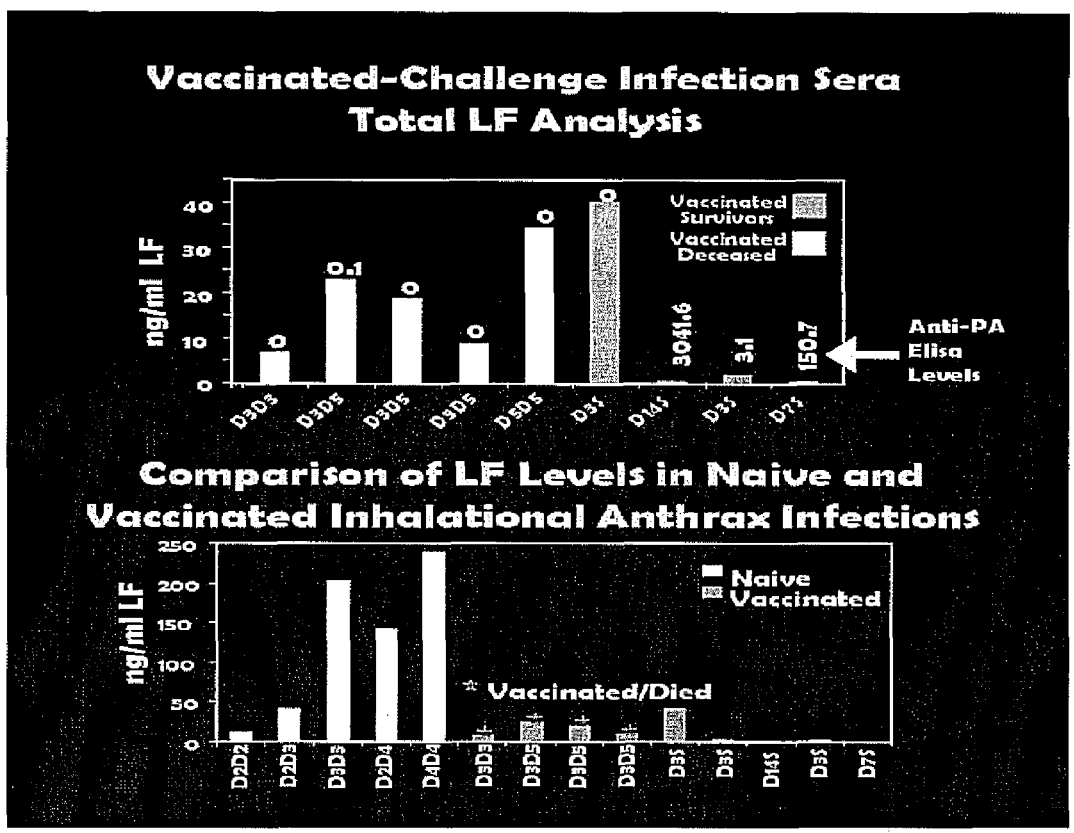
FIG. 12 is bar graphs depicting LF levels in vaccinated animals following challenge by intranasal anthrax infection, with activity levels of LF determined by the present invention in animals previously vaccinated or naïve being compared; vaccinated animals display nearly 10-fold reductions in LF activity levels in serum relative to naïve animals and vaccinated survivors showing nearly 10-fold less LF activity level in serum than deceased animals. The numerical codes along plot x-axes correspond to individual animal codes.
Figure 14:
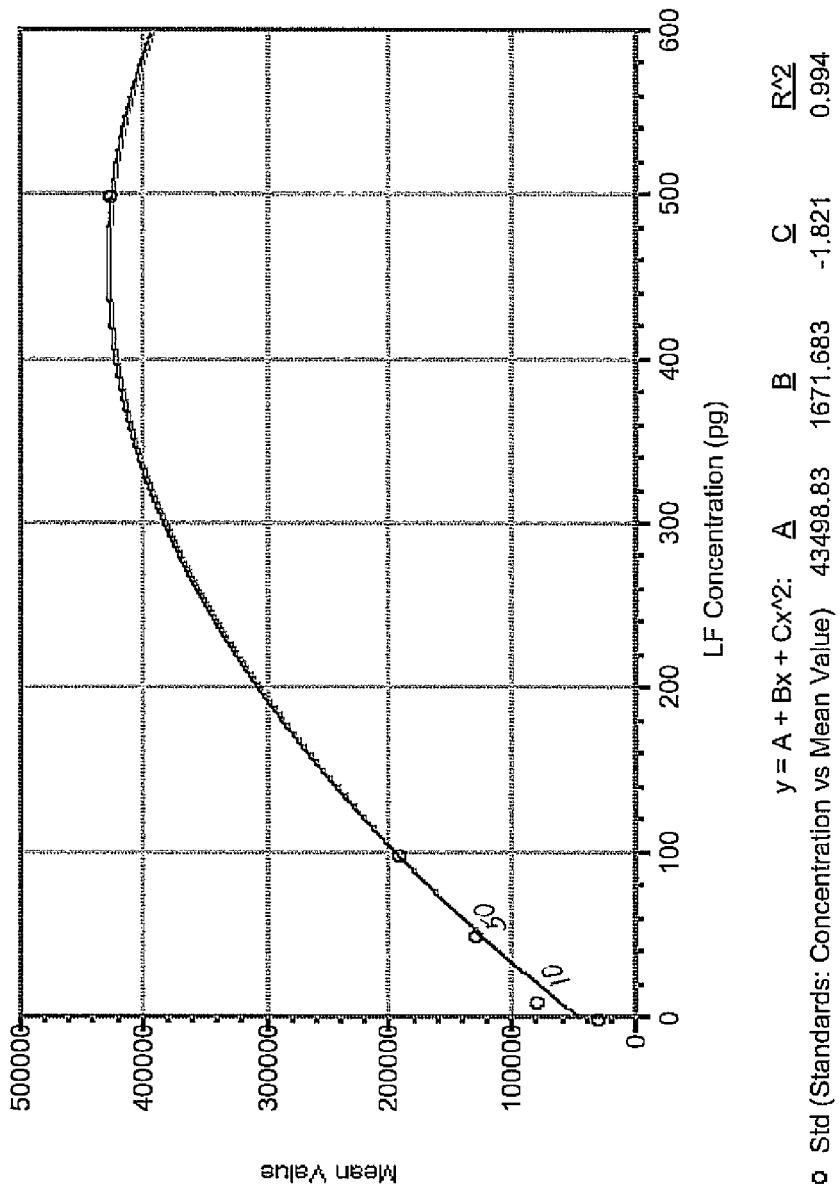
FIG. 14 is a standard curve of LF spiked in serum retrieved using LF-MABs followed by cleavage reaction with FRET-LF substrate.

Analysis of Vaccine Efficacy in an Animal Model of *B. anthracis* Inhalation Infection A murine model of vaccine induced protection are employed essentially as described by Peachman K. K. et al. (2006), *Infection and Immunity*, 74:794-797. Female CBA/J mice (6 weeks old; 15/group) are purchased from the Jackson Laboratory (Bar Harbor, Me.) and maintained with food and water ad libitum. Positive-control mice are immunized by i.m. injection with 20 μg of rPA mixed with alum. Animals are immunized at week 0 and boosted at weeks 2 and 4. Animals are bled at 2-week intervals, and sera analyzed for rPA specific immunoglobulin G (IgG) by ELISA or for toxin-neutralizing antibodies as measured by the dilution of antiserum required for 50% reduction in cellular cytotoxicity (ED$_{50}$). At week 9 post-immunization the mice are challenged by the intranasal route with 234,000 spores (10-50% lethal doses) of *B. anthracis* Ames spores administered in a 50 μl volume in the nasal cavity with a pipette. Biological samples of blood serum are obtained at day zero and each day until mortality or a maximum of 14 days post infection. Samples are processed by the present inventive method and subjected to identification and quantitation by MALDI-TOF. Prior immunization results in decreased levels of free LF in the serum of both survivors and non-survivors at mortality, as shown in FIG. 12, upper panel. However, the levels of free LF will generally be much lower in vaccinated survivors than the deceased group. Similarly, levels of free LF are lower in deceased animals that have been vaccinated relative to the survivors group, as shown in FIG. 12, lower panel.

Example 16

Detection and Quantitation of LF and LTx in a Human Patient with Inhalation Anthrax Biological samples of whole blood, serum, plasma, or pleural fluid is obtained upon hospitalization or as early as possible following a known or possible exposure to anthrax. Quantitation of biological sample LF or LTx levels is performed using the inventive method employing MABs specific for LF or PA and analyzed using MALDI-TOF MS. Levels of LF in excess of 200 ng/ml are detected in plasma or serum at day 4 post symptomatic, as shown in FIG. 13. These levels are confirmed in patient pleural fluid. Plasma/serum samples are obtained each day following hospitalization and levels of LF will decrease with time, as also shown in FIG. 13, right panel. Free LF levels in plasma/serum and pleural fluid decrease at a similar rate, also as shown in FIG. 13, right panel. Similarly, levels of LTx will be detected at day 4 post symptomatic and will be monitored with time. *B. anthracis* infection is confirmed in FIG. 13, right panel, using traditional diagnostic techniques at day 8 post symptomatic indicating that the present inventive method identifies infection at a much earlier time point such that proper treatment may begin sooner increasing chances for survival.

Example 17

Peptide Substrate Synthesis

Synthesis of peptide substrates is performed as described generally by Cummings R. T. et al. (2002), *PNAS USA*, 99:6603-6606. Briefly, an ABI Model 433A peptide synthesizer is employed using FastMoc chemistry including increased acylation times on a 250 µM scale. Suitable reagents will be obtained from PE Applied Biosystems, Polymer Laboratories (Amherst, Mass.) and Molecular Probes (Eugene, Oreg.).

Molecular reporter groups are optionally added to a peptide substrate on resin following peptide synthesis. Incorporation of materials at the N terminus will be accomplished by labeling with the commercially available N-hydroxysuccinimidyl esters. Typical reactions will be performed on a 20-100-µmol resin scale with a 1-10-fold excess of the label in a minimal volume (1-3 ml) of N-methylpyrrolidinone overnight. Incorporation of the two reporters for the FRET substrates will be accomplished by first labeling the N-terminus. The second reporter will then be introduced by selectively removing the Lys(Mtt)-protecting group ($CH_2Cl_2$ with 2% trifluoroacetic acid and 3% triisopropylsilane, room temperature, 45 min), resin washing, and reaction with the label as described above. Dabcyl-Edans FRET substrates are commercially available from www.emdbiosciences.com/novabiochem and www.anaspec.com.

After incorporation of appropriate reporters, the resin will be washed with NMP, acetic acid, $CH_2Cl_2$, and methanol (3 times each), dried briefly in vacuo, and the peptides cleaved with 95% trifluoroacetic acid/2.5% $H_2O$/2.5% triisopropylsilane for 90 min. After precipitation from cold diethyl ether, the crude peptides will be purified on a Waters PrepLC 4000 system with a 25×400 mm 300 Å DeltaPak $C_{18}$ column and a $CH_3CN/H_2O$ gradient (both with 0.1% trifluoroacetic acid). Purified peptides will then be lyophilized and their molecular weight confirmed by mass spectral analysis. All peptides will be >95% pure by RP-HPLC ($A_{214}$).

Example 18

Mouse Toxemia Model

Screening of LF inhibitor candidates will be performed in mice employing a toxemia model as described by Shoop et al. (2005), *PNAS USA*, 102:7958-7963. BALB/c mice (weight, 22 g; age 8 wk) will be used. 32 mice will be allocated at random to one of four groups and each of the four groups then allocated at random to treatment with candidate LF inhibitor at 0, 1, 10, or 30 mg/kg three times a day (t.i.d.) (−0.25, +1, and +3 hours relative to administration of LF and PA), with vehicle. At time 0, all mice will be coinjected i.v. with 100 µg of recombinant LF and 100 µg of recombinant PA in a 150 µl saline mixture into the mouse tail vein and blood serum samples will be obtained for analysis. 10 µl of murine serum will be subjected to analysis by the inventive method and LF activity measured by MALDI-TOF as described above.

Example 19

LF Inhibitor Screening in Rabbit Inhalation Infection Model

Screening of LF inhibitor candidates will be performed in rabbits following infection with Ames spores as described by Shoop et al. (2005), *PNAS USA*, 102:7958-7963. Dutch belted (DB) rabbits (weight, 2 kg; age, 16 wk) purchased from Covance (Princeton, N.J.) will be used. Six DB rabbits will be dosed s.c. with LF inhibitor at 100 mg/kg t.i.d. in saline for 7 days and six rabbits dosed s.c. with saline at the same times. Two hours after the first dose, all rabbits will be challenged s.c. with $10^4$ *B. anthracis* Ames spores and observed for 21 days. At time 0, and each day for 21 days blood serum will be obtained. 10 µl of murine serum from each time point will be subjected to analysis by the inventive method and LF activity measured by MALDI-TOF as described above.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process for detecting an anthrax lethal factor in a biological sample comprising:
   isolating and concentrating the anthrax lethal factor from the biological sample;
   reacting the anthrax lethal factor with a peptide substrate cleaved by said anthrax lethal factor to yield a substrate cleavage product; and
   detecting said cleavage product of said peptide substrate to detect said anthrax lethal factor in the biological sample.

2. The process of claim 1 further comprising quantitating said cleavage product.

3. The process of claim 1 wherein said anthrax lethal factor is selected from the group consisting of: *Bacillus anthracis* lethal factor and *Bacillus anthracis* lethal toxin.

4. The process of claim 1 wherein said anthrax lethal factor is isolated and concentrated by binding to beads coupled with an antibody specific to the anthrax lethal factor.

5. The process of claim 4 wherein said beads are magnetic.

6. The process of claim 1 wherein said peptide substrate is a member of the mitogen-activated protein kinase kinase family.

7. The process of claim 1 wherein said peptide substrate contains a fluorophore and a fluorescence quenching molecule.

8. The process of claim 1 wherein said peptide substrate contains a fluorophore.

9. The process of claim 1 wherein said peptide substrate contains a light absorbing molecule.

10. The process of claim 1 wherein said biological sample is derived from a mammal.

11. The process of claim 1 wherein said biological sample is derived from a human.

12. The process of claim 1 wherein said biological sample is selected from the group consisting of: whole blood, plasma, serum, extracellular fluid, cytosolic fluid, and tissue.

13. The process of claim 1 wherein the lethal factor is anthrax lethal toxin and said isolating and concentrating said anthrax lethal toxin is performed by adsorption to a solid substrate.

14. The process of claim 1 wherein said peptide substrate is comprised of the sequence Seq. Nos. 2, 3, 4, 5, 6, 7, 15, 16, 17, and 18.

15. The process of claim 4, wherein said antibody is derived from an organism selected from the group comprising a: mammal, human, mouse, rabbit, monkey, donkey, horse, rat, swine, cat, chicken, goat, guinea pig, hamster, and sheep.

16. The process of claim 1 wherein said peptide substrate contains a molecule selected from the group comprising: biotin, avidin, horseradish peroxidase, streptavidin, and digoxin.

17. The process of claim 4, wherein said antibody is selected from the group comprising: monoclonal and polyclonal.

18. The process of claim 4, wherein said antibody recognizes a *Bacillus anthracis* protein selected from the group comprising: protective antigen, lethal toxin, lethal factor and edema factor.

19. The process of claim 1 wherein said detection process is selected from the group comprising: mass spectrometry, fluorescence resonance energy transfer, fluorescence, light absorption, enzyme linked immuno-adsorbant assay, coupled enzyme assay, continuous enzyme assay, discontinuous enzyme assay, flow cytometry, FLIPR, high-performance liquid chromatography, and colorimetric assay.

20. The process of claim 1 further comprising quantitating said lethal factor present in said biological sample by comparison of said formation rate to a standard curve.

* * * * *